US008849579B2

(12) United States Patent
Mai et al.

(10) Patent No.: US 8,849,579 B2
(45) Date of Patent: Sep. 30, 2014

(54) METHODS OF DETECTING AND MONITORING CANCER USING 3D ANALYSIS OF CENTROMERES

(75) Inventors: Sabine Mai, Winnipeg (CA); Yuval Garini, Misgav (IL); Rahul Sarkar, Winnipeg (CA); Bartholomeus J. Vermolen, Enschede (NL)

(73) Assignee: 3D Signatures Inc., Winnipeg (CA)

( * ) Notice: Subject to any disclaimer, the term of this patent is extended or adjusted under 35 U.S.C. 154(b) by 843 days.

(21) Appl. No.: 12/443,781

(22) PCT Filed: Sep. 28, 2007

(86) PCT No.: PCT/CA2007/001730
§ 371 (c)(1),
(2), (4) Date: Jan. 7, 2010

(87) PCT Pub. No.: WO2008/040116
PCT Pub. Date: Apr. 10, 2008

(65) Prior Publication Data
US 2010/0143903 A1    Jun. 10, 2010

Related U.S. Application Data

(60) Provisional application No. 60/848,746, filed on Oct. 2, 2006.

(51) Int. Cl.
*G06F 19/00* (2011.01)
*G01N 33/574* (2006.01)
*C12Q 1/68* (2006.01)
*G06K 9/00* (2006.01)
*G01N 33/50* (2006.01)
*G01N 15/14* (2006.01)

(52) U.S. Cl.
CPC ............ *G06F 19/345* (2013.01); *G06K 9/0014* (2013.01); *C12Q 1/6886* (2013.01); *G01N 33/57426* (2013.01); *G01N 33/5091* (2013.01); *G01N 15/1475* (2013.01); *G01N 33/5035* (2013.01); *G01N 33/574* (2013.01)
USPC ............................ 702/19; 435/6.14; 435/7.23

(58) Field of Classification Search
CPC ............ G06F 19/345; G06K 9/00127–9/00147
See application file for complete search history.

(56) References Cited

U.S. PATENT DOCUMENTS

| 6,506,563 B1 | 1/2003 | Speicher et al. | |
|---|---|---|---|
| 2002/0012472 A1* | 1/2002 | Waterfall et al. | 382/245 |
| 2007/0031831 A1 | 2/2007 | Mai et al. | |

OTHER PUBLICATIONS

Gehrke, I., Garini, Y. & Mai, S. Three dimensional (3D) analysis of centromere organization in interphase nuclei of normal and tumor cells. AACR Meeting Abstracts 2005, 30 (2005).*

Kozubek, M., Matula, P., Matula, P. & Kozubek, S. Automated acquisition and processing of multidimensional image data in confocal in vivo microscopy. Microscopy Research and Technique 64, 164-175 (2004).*

(Continued)

*Primary Examiner* — Soren Harward
(74) *Attorney, Agent, or Firm* — Kathleen D. Rigaut; Robert C. Netter, Jr.; Dann, Dorfman, Herrell & Skillman

(57) ABSTRACT

The present application relates to a method of detecting and monitoring cancer or precancer in a cell using three-dimensional analysis to assess centromere organization. In addition, the application relates to a method and system for characterizing the 3D organization of centromeres.

19 Claims, 15 Drawing Sheets

(56) References Cited

OTHER PUBLICATIONS

Kozubek, M. et al. Combined confocal and wide-field high-resolution cytometry of fluorescent in situ hybridization-stained cells. Cytometry 45, 1-12 (2001).*
McDonald, J. H. Handbook of Biological Statistics. (2008). Excerpt of pp. 153-160.*
Shapiro, D. E. The interpretation of diagnostic tests. Statistical Methods in Medical Research 8, 113-134 (1999).*
Spitalnic, S. Test Properties 2: Likelihood Ratios, Bayes' Formula, and Receiver Operating Characteristic Curves. Hospital Physician 40, 53-58 (2004).*
Statistical analysis of data presented in instant Fig. 1, panel B, performed by the examiner. Comprises 3 figures and 1 page listing of R source code.*
U.S. Cancer Statistics Working Group. United States Cancer Statistics: 1999-2009 Incidence and Mortality Web-based Report. Atlanta: U.S. Department of Health and Human Services, Centers for Disease Control and Prevention and National Cancer Institute; 2013. Available at: www.cdc.gov/uscs. Retrieved Sep. 10, 2013.*
Tripathy, D. & Rubenstein, J. "Neoplasia". Chapter 5 of Pathophysiology of Disease: An Introduction to Clinical Medicine. Fourth Edition. (McPhee, S. J., Lingappa, V. R. & Ganong, W. F.) 91-112 (McGraw-Hill Professional, 2002).*
Aubele, M. et al. "Comparative FISH analysis of numerical chromosome 7 abnormalities in 5-µm paraffin-embedded tissue sections from prostatic carcinoma". Histochem. Cell Biol. Feb. 1997, vol. 107, No. 2, p. 121-126.
Beil, M. et al. "Spatial distribution patterns of interphase centromeres during retinoic acid-induced differentiation of promyelocytic leukemia cells". Cytometry, Apr. 1, 2002, vol. 47, No. 4, p. 217-225.
Beil, M. et al. "Statistical analysis of the three-dimensional structure of centromeric heterochromatin in interphase nuclei". J. Microsc, Jan. 2005, vol. 217, Pt. 1, p. 60-68.
Garagna, S. et al. "Three-dimensional localization and dynamics of centromeres in mouse oocytes during folliculogenesis". J. Mol. Histol. Aug. 2004, vol. 35, No. 6, p. 631-638.
Kuroda, M. et al. "Alterationo f chromosome positioning during adipocyte differentiation". J. Cell Sci. Nov. 15, 2004, vol. 117, Pt. 24, p. 5897-5903.
Tagawa, Y. et al. "Differences in Spatial localization and chromatin pattern during different phases of cell cycle between normal and cancer cells". Cytometry. Apr. 1, 1997, vol. 27, No. 4, p. 327-335.
Wiblin, A.E. et al. "Distinctive nuclear organisation of centromeres and regions involved in pluripotency in human embryonic stem cells". J. Cell Sci., Sep. 1, 2005, vol. 118, Pt. 17, p. 3861-3868.
Toland C F et al: "3D organisation of chromosome 11 centromeres in prostate cancer cell lines" Cellular Oncology vol. 27, No. 2, 2005, p. 158.
Koutna I et al: "Topography of genetic loci in tissue samples: towards new diagnostic tool using interphase FISH and high-resolution image analysis techniques." Analytical Cellular Pathology : The Journal of the European Society for Analytical Cellular Pathology 2000, vol. 20, No. 4, 2000, pp. 173-185.
Solovei Irina et al: "Differences in centromere positioning of cycling and postmitotic human cell types" Chromosoma (Berlin), vol. 112, No. 8, Jun. 2004, pp. 410-423.
Bayani Jane et al: "Spectral karyotyping identifies recurrent complex rearrangements of chromosomes 8, 17, and 20 in osteosarcomas." Genes Chromosomes and Cancer, vol. 36, No. 1, Jan. 2003, pp. 7-16.
Beheshti et al: "Identification of a high frequency of chromosomal rearrangements in the centromeric regions of prostate cancer cell lines by sequential Giemsa banding and spectral karyotyping" Molecular Diagnosis, Naperville, IL, US, vol. 5, No. 1, Jan. 1, 2000, pp. 23-32.
Sarkar Rahul et al: "Alterations of centromere positions in nuclei of immortalized and malignant mouse lympocytes." Cytometry. Part A : The Journal of the International Society for Analytical Cytology Jun. 2007, vol. 71, No. 6, Jun. 2007, pp. 386-392.
Guffei Amanda et al: "c-Myc-dependent formation of robertsonian translocation chromosomes in mouse cells" Neoplasia (New York), vol. 9, No. 7, Jul. 2007, p. 578.
Goncalves Dos Santos Silva Amanda et al: "Centromeres in cell division, evolution, nuclear organization and disease." Journal of Cellular Biochemistry Aug. 15, 2008, vol. 104, No. 6, Aug. 15, 2008, pp. 2040-2058.
Chuang T C Y et al: "The three-dimensional organization of telomeres in the nucleus of mammalian cells" (2004) BMC Biol. 2:12-20.
Louis S F et al: "c-Myc induces chromosomal rearrangements through telomere and chromosome remodeling in the interphase nucleus" (2005) Proc. Natl. Acad. Sci USA. 102(27):9613-8.
Vermolen B J et al: "Characterizing the Three-Dimensional Organization of Telomeres" (2005) Cytometry A. 67A:144-50.
Mai S et al: "Oncogenic Remodeling of the Three-Dimensional Organization of the Interphase Nucleus" (2005) Cell Cycle. 4(10):1327-1331.
Mai S et al: "The Significance of Telomeric Aggregates in the Interphase Nuclei of Tumor Cells" (2006) Journal of Cellular Biochemistry. 97:904-15.
Maierhofer Christine et al: "Multicolor deconvolution microscopy of thick biological specimens" American Journal of Pathology. Feb. 2003, vol. 162, No. 2, Feb. 1, 2003, pp. 373-379.
Henderson S et al: "In situ analysis of changes in telomere size during replicative aging and cell transformation" The Journal of Cell Biology, Rockefeller University Press, US, vol. 134, No. 1, Jul. 1996, pp. 1-12.
Schaefer L H et al: "Generalized approach for accelerated maximum likelihood based image restoration applied to three-dimensional fluorescence microscopy." Journal of Microscopy. Nov. 2001, vol. 204, No. Pt 2, Nov. 2001, pp. 99-107.
Bass Hank W et al: "Telomeres cluster de novo before the initiation of synapsis: A three-dimensional spatial analysis of telomere positions before and during meiotic prophase" Journal of Cell Biology, vol. 137, No. 1, 1997, pp. 5-18.
Weierich Claudia et al: "Three-dimensional arrangements of centromeres and telomeres in nuclei of human and murine lymphocytes." Chromosome Research, vol. 11, No. 5, May 2003, pp. 485-502.
Raz V et al: "Changes in lamina structure are followed by spatial reorganization of heterochromatic regions in caspase-8-activated human mesenchymal stem cells", Journal of Cell Science 119(20), Sep. 26, 2006, pp. 4247-4256.
Gonzalez-Suarez I et al: "Novel roles for A-type lamins in telomere biology and the DNA damage response pathway", The EMBO Journal (2009) 28, pp. 2414-2427.

* cited by examiner

Panel A

Panel B

Panel C

Panel D

Panel F

Panel G

SEQUENCE LISTING

<160> NUMBER OF SEQ ID NOS: 4

<210> SEQ ID NO 1
<211> LENGTH: 17
<212> TYPE: DNA
<213> ORGANISM: Artificial Sequence
<220> FEATURE:
<223> OTHER INFORMATION: PNA Centromere Probe

<400> SEQUENCE: 1
attcgttgga aacggga                                                      17

<210> SEQ ID NO 2
<211> LENGTH: 18
<212> TYPE: DNA
<213> ORGANISM: Artificial Sequence
<220> FEATURE:
<223> OTHER INFORMATION: PNA Centromere Probe

<400> SEQUENCE: 2
cacaaagaag tttctgag                                                     18

<210> SEQ ID NO 3
<211> LENGTH: 18
<212> TYPE: DNA
<213> ORGANISM: Artificial Sequence
<220> FEATURE:
<223> OTHER INFORMATION: PNA Centromere Probe

<400> SEQUENCE: 3
cagacagaag cattctca                                                     18

<210> SEQ ID NO 4
<211> LENGTH: 18
<212> TYPE: DNA
<213> ORGANISM: Artificial Sequence
<220> FEATURE:
<223> OTHER INFORMATION: PNA Centromere Probe

<400> SEQUENCE: 4
tgcattcaac tcacagag                                                     18

METHODS OF DETECTING AND MONITORING CANCER USING 3D ANALYSIS OF CENTROMERES

This application is a §371 application which claims priority to PCT/CA2007/001730 filed Sep. 28, 2007, which in turn claims priority to U.S. Provisional Application 60/848,746 filed Oct. 2, 2006, each of the foregoing applications being incorporated herein by reference as though set forth in full.

FIELD OF THE INVENTION

The present application relates to methods of detecting and monitoring cancer in a cell, in particular the use of three-dimensional (3D) analysis to characterize the organization of centromeres in a cell.

BACKGROUND OF THE INVENTION

The three-dimensional (3D) organization of the nucleus has been shown to be important in genomic stability [Zink D, Fischer A H, Nickerson J A: Nuclear structure in cancer cells. (2004)*Nat Rev Cancer,* 4:677-687], and any change(s) in this organization potentially cause genomic instability [Mai S, Garini Y: Oncogenic remodeling of the three-dimensional organization of the interphase nucleus: c-Myc induces telomeric aggregates whose formation precedes chromosomal rearrangements. (2005) *Cell Cycle,* 4:1327-1331. Epub Oct. 5, 2005; Mai S and Garini Y: The significance of telomeric aggregates in the interphase nuclei of tumor cells. (2006) *J Cell Biochem,* 97:904-915. Review].

At present, there is inexact knowledge of about the 3D organization of centromeres in normal, immortalized and tumor cells. However, this knowledge is of fundamental importance to the structural and functional organization of the normal nucleus and to the puzzle of genomic instability in tumor cells.

Previous studies reported on a dynamic organization of centromeres during the cell cycle [Solovei I, Schermelleh L, During K, Engelhardt A, Stein S, Cremer C, Cremer T: Differences in centromere positioning of cycling and postmitotic human cell types. (2004) *Chromosoma,* 112:410-423. Epub Jun. 9, 2004], during folliculogenesis of mouse oocytes [Garagna S, Merico V, Sebastiano V, Monti M, Orlandini G, Gatti R, Scandroglio R, Redi C A, Zuccotti M: Three-dimensional localization and dynamics of centromeres in mouse oocytes during folliculogenesis. (2004) *J Mol Histol,* 35:631-638] and during differentiation of human embryonic stem cells [Wiblin A E, Cui W, Clark A J, Bickmore W A: Distinctive nuclear organisation of centromeres and regions involved in pluripotency in human embryonic stem cells. (2005) *J Cell Sci,* 118(Pt 17):3861-3868. Epub Aug. 16, 2005]. However, centromeric changes during cellular immortalization and transformation have not been previously examined.

SUMMARY OF THE INVENTION

The present inventors have elucidated the three-dimensional (3D) organization and localization of centromeres in the nuclei of normal, immortalized and tumor cells. The inventors have shown that centromeres are organized dynamically and non-randomly in the 3D nucleus of normal cells, and that centromere organization is altered in immortalized and cancer cells. This altered centromere organization allows chromosomal rearrangements, which are commonly associated with cancer.

The method disclosed in the present application has advantages over methods in the prior art including methods that assess telomeric and/or chromosome organization in cancer cells. In particular, the methods described herein can detect alterations in centromere organization in cells in earlier stages of the transformation process, such as precancerous cells.

Specifically, the inventors have discovered that centromeres are more peripherally located in the nuclei of normal cells, less peripherally located in the nuclei of immortalized cells and even more less peripherally located in the nuclei of cancer cells. Thus, the 3D organization of centromeres can be used to detect, diagnose or monitor cancer or precancer.

Accordingly, the present application relates to a method of detecting or monitoring cancer or precancer in a test cell from a subject comprising the steps:
(a) characterizing centromere organization in the test cell using three-dimensional (3D) analysis; and
(b) comparing the centromere organization in the test cell with the centromere organization of a control cell,
wherein the comparison between the centromere organization of the test cell and the centromere organization of the control cell is used to detect or monitor cancer.

For example, if there is a difference in centromere organization in the test cell compared to the control cell and the control cell is a normal, disease-free cell, then this indicates the presence of cancer or precancer.

The method disclosed herein may be used to detect or monitor disease, radiation and environmental exposure, and DNA repair and response in a cell. In particular the method disclosed herein may be used to detect, monitor or diagnose cancer. In addition, the method disclosed herein may be used to monitor disease treatment, in particular cancer treatment.

In addition, a method and system for characterizing the 3D organization of centromeres are described herein. The system includes an input module for inputting image data of the 3D organization of centromeres and a characteristic module for finding a parameter of the 3D organization therefrom. In particular, the parameters include a set of distances of the centromere(s) from the nuclear center, a set of distances of the centromere(s) from the nuclear border, and/or the relative position of the centromere(s) from the nuclear center to the nuclear border. The parameters can also include average and standard deviation of the sets of distances.

Each of these parameters to characterize the 3D organization of centromeres may be used for several purposes, including to monitor or detect cancer in a cell and to monitor cancer treatment.

Other features and advantages of the present invention will become apparent from the following detailed description. It should be understood, however, that the detailed description and the specific examples while indicating preferred embodiments of the invention are given by way of illustration only, since various changes and modifications within the spirit and scope of the invention will become apparent to those skilled in the art from this detailed description.

BRIEF DESCRIPTION OF THE DRAWINGS

The invention will now be described in relation to the drawings in which.

DETAILED DESCRIPTION OF THE INVENTION

Figure 1:
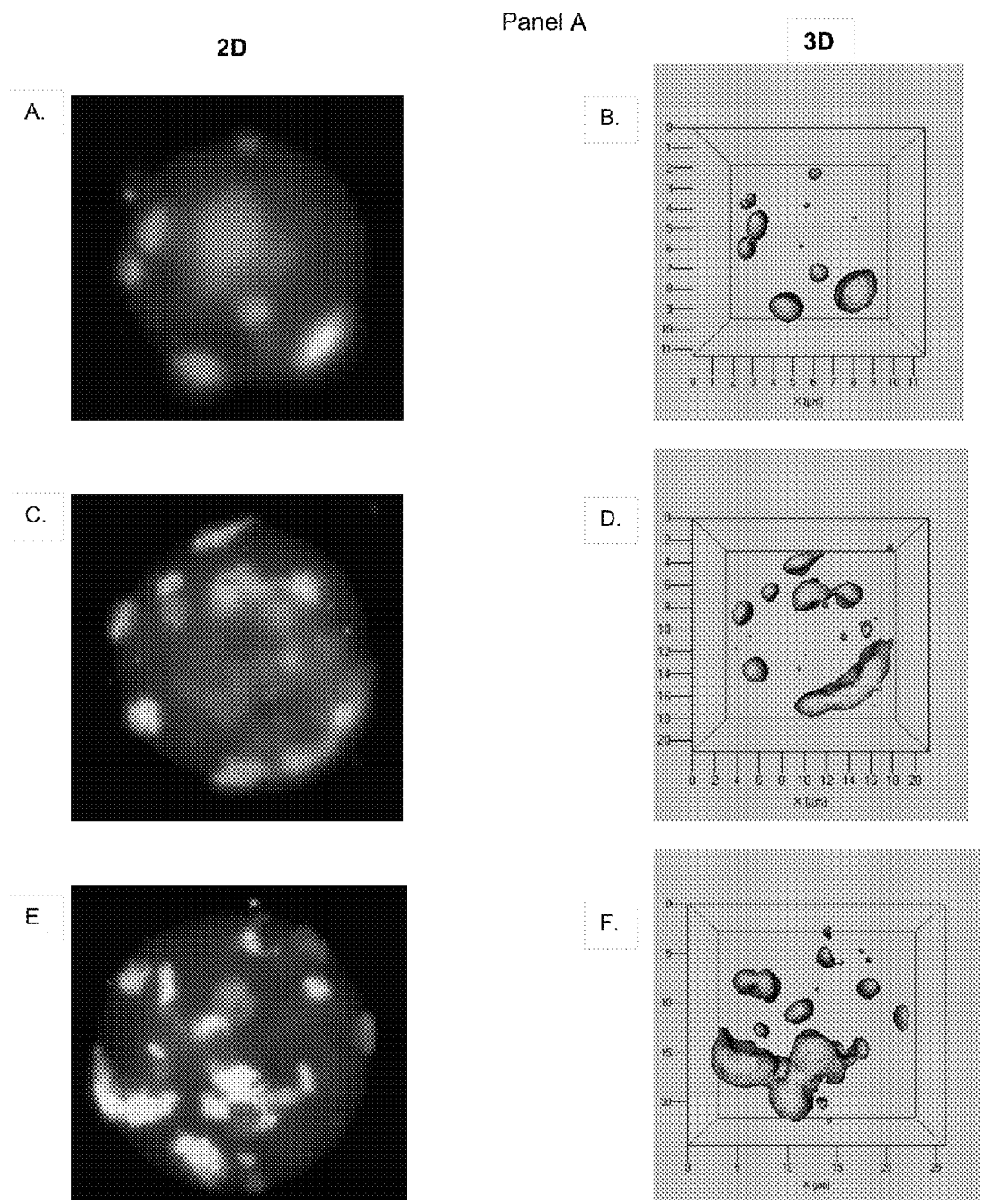
FIG. 1 shows centromere distribution patterns and frequencies in primary lymphocytes, immortalized PreB cells and mouse plasmacytoma cells (MOPC460D). Panel A. Two-dimensional (2D) and three-dimensional (3D) images of representative nuclei from primary mouse lymphocytes (a and b), immortalized PreB (c and d), and MOPC460D cells (e and f) showing qualitative analyses of centromere distribution patterns. Centromeres are shown in green, nuclei are shown in blue. Image acquisition was carried out as described in Methods. Panel B. Overview graphs of the corresponding samples that are shown as representative images in Panel A. Each graph is based on 147 nuclei that were acquired by 3D imaging, deconvolved using the constrained iterative algorithm [Schaefer L H, Schuster D. and Herz H: Generalized approach for accelerated maximum likelihood based image restoration applied to three-dimensional fluorescence microscopy. (2001) *J Microsc*, 204:99-107], and then analyzed in CentroView™ as described in Methods. a) Overview graph of centromeric frequency distribution along a radial nuclear axis for primary lymphocytes from T38HxBalb/c mice. b) Overview graph of centromeric frequency distribution along a radial nuclear axis for immortalized PreB cells. c) Overview graph of centromeric frequency distribution along a radial nuclear axis for nuclei of MOPC460D cells.
Figure 1:
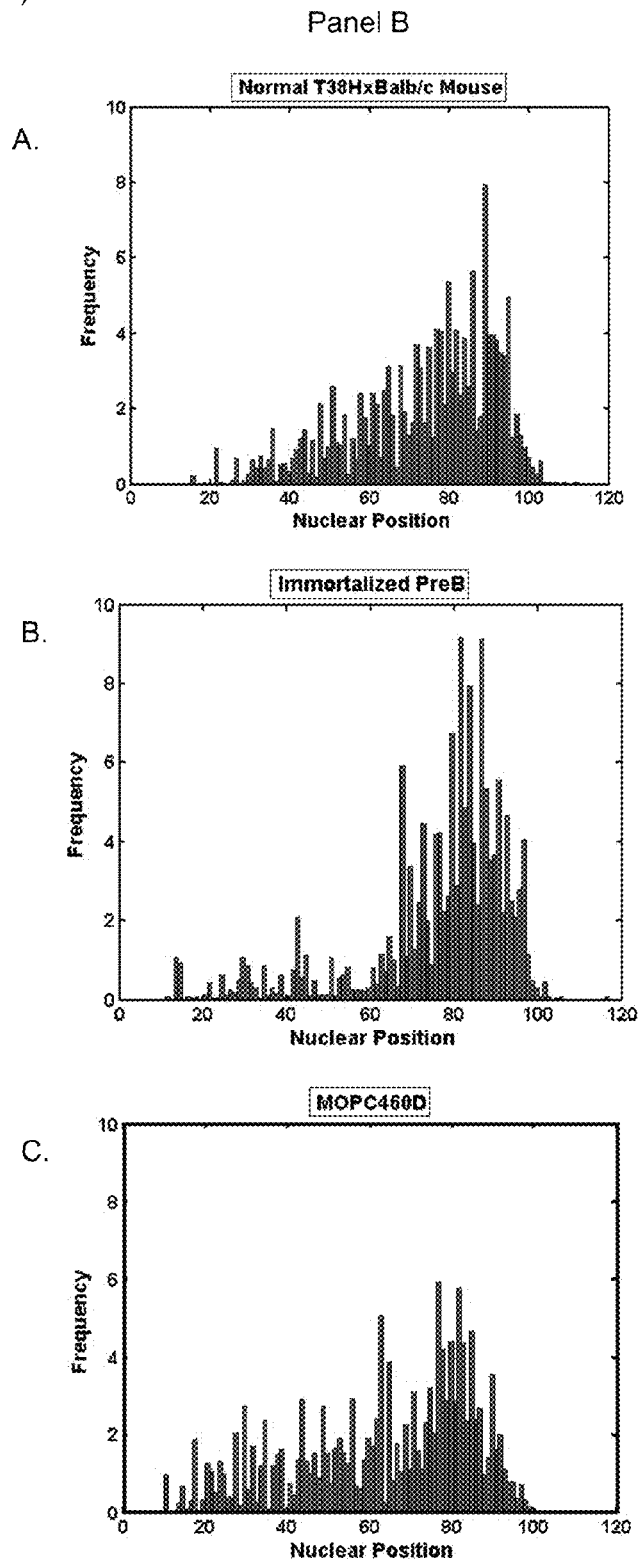

The present inventors have used high-resolution deconvolution microscopy and imaging to elucidate the three-dimensional (3D) organization of centromeres in nuclei of normal, immortalized and cancer cells. The inventors found that centromeres from tumor and immortalized cells have a different 3D organization than normal cells. Thus, the 3D organization of centromeres can be used to detect, diagnose or monitor cancer or precancer.

Accordingly, the present application relates to a method of detecting or monitoring cancer or precancer in a test cell from a subject comprising the steps:
 (a) characterizing centromere organization in the test cell using three-dimensional (3D) analysis; and
 (b) comparing the centromere organization in the test cell with the centromere organization of a control cell,
wherein the comparison between the centromere organization of the test cell and the centromere organization of the control cell is used to detect or monitor cancer.

For example, if there is a difference in centromere organization in the test cell compared to the control cell and the control cell is a normal, disease-free cell, then this indicates the presence of cancer or precancer.

As mentioned above, the inventors have discovered that centromeres are more peripherally located in the nuclei of normal cells, less peripherally located in the nuclei of immortalized cells and even more less peripherally located in the nuclei of cancer cells. In other words, the inventors have discovered that centromeres are more centrally located in the nuclei of cancer cells, less centrally located in the nuclei of immortalized cells and even more less centrally located in the nuclei of normal cells.

A person skilled in the art will appreciate that centromere organization or positioning of the centromeres in the nucleus can be characterized in several ways. For example, sets of distances of the centromeres can be measured relative to the nuclear centre or can be measured relative to the nuclear border. In addition, relative distances of the centromeres can be defined in reference to the nuclear center and the nuclear border. For example, centromeric distribution can be defined in terms of percentage increments from 0 to 100, with 0% being the nuclear center and 100% being the nuclear border. Thus, centromeres can be characterized as "peripherally located" if they are closer to the nuclear border than the nuclear center, or if they have measured percentage increment closer to 100%. Centromeres can be characterized as "centrally located" if they are closer to the nuclear center than the nuclear border, or if they have measured percentage increments closer to 0%.

The phrase "detecting or monitoring cancer or precancer" as used herein refers to a method or process of determining if a subject has or does not have cancer or a precancerous condition, or determining the severity or degree of cancer or precancerous condition.

As used herein, the term "cell" includes more than one cell or a plurality of cells or portions of cells.

The sample or "test cell" may be from any member of the animal kingdom, in particular from mammals, more particularly from humans, and may be, without limitation, biological fluids (such as blood, serum, lymphatic, saliva or cerebrospinal fluid), tissue, hair or organ. An advantage of the method disclosed in the present application is that only a very thin slice or section of a tissue (even thinner than the width of a cell) is needed.

The term "subject" as used herein refers to any member of the animal kingdom, preferably a mammal, more preferably a human being. In a preferred embodiment, the subject is suspected of having or has cancer.

In embodiments, the "test cell" is a cell from a subject that is suspected of having a cell-proliferative disorder such as cancer or precancerous condition. In such an embodiment, the test cell includes, but is not limited to, a cancer cell or a precancerous cell. The term cancer includes any cancer including, without limitation, cervical cancer, ovarian cancer, pancreatic cancer, head and neck cancer, squamous cell carcinoma, gastrointestinal cancer, bladder cancer, breast cancer (such as carcinoma, ductal, lobular, and nipple), prostate cancer, non small cell lung cancer, Non-Hodgkin's lymphoma, multiple myeloma, leukemia (such as acute lymphocytic leukemia, chronic lymphocytic leukemia, acute myelogenous leukemia, and chronic myelogenous leukemia), brain cancer, neuroblastoma, sarcomas, colon cancer, plasmacytoma, head and neck squamous cell carcinoma, lymphoma, and cMyc-dependent tumors. In another embodiment, the cancer includes, without limitation, lymphoma, plasmascytoma and cMyc-dependent cancer. In a further embodiment, the cancer includes, without limitation, B cell lymphoma, plasmacytoma and a B cell cancer that is cMyc-dependent. When monitoring or detecting cancer or precancer, the sample containing the test cell can be any sample that potentially contains the cancerous or precancerous cells, such as a biopsy from the tumor, a blood sample or lymphatic fluid sample.

As used herein, the term "control cell" refers to a cell that is known to be normal and disease-free, or a cell that is known to be an immortalized cell or precancerous cell, or a cell that is known to be a cancer cell. In one embodiment, the control cell is a B lymphocyte that is known to be normal and disease-free.

A person skilled in the art will appreciate that the comparison between centromere organization of the test cell and centromere organization of the control cell to detect or monitor cancer will depend on the control cell used. For example, if the control cell is a normal and disease-free cell, and the centromeres of the test cell are more centrally located in the nucleus as compared to the centromeres of the control cell, then this is indicative of cancer or a precancerous cell. For example, if the control cell is a cancer or precancerous cell, and the centromeres of the test cell are more peripherally located in the nucleus as compared to the centromeres of the control cell, then this is not indicative of cancer or a precancerous cell.

A person skilled in the art will appreciate that the control can also be a pre-determined standard.

The term "three-dimensional (3D) analysis" as used herein refers to any technique that allows the 3D visualization of cells, for example high-resolution deconvolution microscopy. In an embodiment, the 3D analysis is performed using the system described herein.

The term "centromere organization" as used herein refers to the 3D arrangement of a centromere or more than one centromere or a region of centromeres, in a cell during any phase of the cell cycle. In particular, the term refers to the distance of a centromere or more than one centromere or a region of centromeres relative to the nuclear center or relative to the nuclear border, or the distribution of the distances between the centromeres and the nuclear center and/or nuclear boarder. The method disclosed herein has the advantage that the global positioning of all the centromeres in the test cell can be characterized simultaneously, for example with pan-centromeric probes. As mentioned above, the characterization of centromere organization can be done in any phase of the cell cycle, and a person skilled in the art will appreciate that the phase of the cell cycle is taken into account in the analysis.

The term "nuclear center" refers to the central region of a nucleus. The term "nuclear border" refers to the peripheral region of a nucleus.

The method disclosed herein may also be used to monitor disease treatment. For example, samples comprising test cell(s) from a patient with a cell proliferative disorder may be taken at various time points, for example before, during and after chemo or other forms of therapy, and the presence of cancer or precancer determined. The diminishing of cancer or precancer in the test cells over time would be indicative of successful therapy. Conversely, an increase in or lack of change in the cancer or precancer of the test cells over time would be indicative of unsuccessful therapy.

Accordingly, the present application further relates to a method of monitoring cancer treatment in a test cell from a subject comprising the steps:
 (a) characterizing centromere organization in the test cell using three-dimensional (3D) analysis; and
 (b) comparing the centromere organization in the test cell with the centromere organization of a control cell,
wherein the comparison between the centromere organization of the test cell and the centromere organization of the control cell is correlated with cancer treatment.

A person skilled in the art will appreciate that the comparison between centromere organization of the test cell and centromere organization of the control cell to monitor cancer treatment will depend on the control cell used. For example, if the test cell is from the same patent as the control cell, but after treatment, and the centromeres of the test cell are more peripherally located in the nucleus as compared to the centromeres of the control cell, then this is indicative of successful therapy. For example, if the test cell is from the same patent as the control cell, but after treatment, and the centromeres of the test cell are more centrally located as compared to the centromeres of the control cell, then this is indicative of unsuccessful therapy.

As used herein, and as well understood in the art, "treatment" is an approach for obtaining beneficial or desired results, including clinical results. Beneficial or desired clinical results can include, but are not limited to, alleviation or amelioration of one or more symptoms or conditions, diminishment of extent of disease, stabilized (i.e. not worsening) state of disease, preventing spread of disease, delay or slowing of disease progression, amelioration or palliation of the disease state, and remission (whether partial or total), whether detectable or undetectable. "Treatment" can also mean prolonging survival as compared to expected survival if not receiving treatment.

"Palliating" a disease or disorder means that the extent and/or undesirable clinical manifestations of a disorder or a disease state are lessened and/or time course of the progression is slowed or lengthened, as compared to not treating the disorder.

The present application also relates to methods and systems for characterizing the 3D organization of centromeres.

The system includes an input module for inputting image data of the 3D organization of centromeres and a characteristic module for finding a parameter of the 3D organization therefrom. In another embodiment, the system can include an input module, an image data processor, an optimizer and/or a characteristic module.

The input module inputs image data of the 3D organization of centromeres. The input module includes appropriate hardware and/or software, such as a CD-ROM and CD-ROM reader, or other data storage and reading means. The inputting performed by the input module need not be from outside the system to inside the system. Rather, in some embodiments, the inputting of data may describe the transfer of data from a permanent storage medium within the system, such as a hard disk of the system 100, to a volatile storage medium of the system, such as RAM.

The image data can be obtained using regular or confocal microscopy and can include the intensities of one or more colors at pixels (totaling, for example, 300×300 or 500×500) that comprise an image of a nucleus. The image data can also be grey level image data of a nucleus that has been appropriately stained to highlight centromeres. Several images (on the order of 100) are obtained corresponding to slices along a particular axis. Thus, the image data may correspond to a total of about $2.5 \times 10^7$ pixels. In one embodiment, the slices may be on the order of 100 nanometers apart. In this manner, the image data accounts for the 3D quality of the organization of centromeres. In addition, the confocal microscope is able to obtain the intensity of two colors, for example blue and green, of the nucleus at every pixel imaged, thereby doubling the amount of data points.

To obtain an image of centromeres, a probe such as Pan Centromeric Probes (Cederlane, UK) can be used. In addition, a stain such as DAPI can be used to preferentially mark the heterochromatin material that comprises DNA.

To improve the quality of the image data, various techniques can be brought to bear as known to those of ordinary skill, such as constrained iterative deconvolution of the image data to improve resolution. Such constrained iterative deconvolution may not be required if confocal, instead of regular, microscopy is used as the image data may be of superior resolution. In addition, other instruments, such as an apotome, may be used to improve the quality of the image.

The image data processor processes the image data to find a set of coordinates $\{(x_i, y_i, z_i)\}$, $i=1, \ldots, N$, where $(x_i, y_i, z_i)$ is a position of the ith centromere. For this purpose, the image data processor identifies "blobs" within the image data that can be identified as a centromere using a segmentation process. Each blob identified as a centromere has a non-negligible volume. There is some freedom, therefore, in choosing "the position" of the centromere. One possibility is to choose for this position the center of mass of the centromere. The segmented image is then used in combination with the DAPI nuclear image to quantify the distance of the centromere with respect to the nuclear center. For example, the center of mass of the nucleus is determined, and then the distance between the center of mass of the centromere to the nuclear center is computed.

The characteristic module can be used to find at least one parameter that can be used to characterize the 3D organization of centromeres. In particular, the parameters include a set of distances of the centromere(s) from the nuclear center, a set of distances of the centromere(s) from the nuclear border, and/or the relative position of the centromere(s) from the nuclear center and the nuclear border. The parameters can also include a set of volumes of the centromeres and/or set of intensities of the centromeres. The sets can be used to calculate statistical measures such as average, median or standard deviation.

Each of these parameters to characterize the 3D organization of centromeres may be used for several purposes, including to monitor or detect cancer in a cell and to monitor cancer treatment.

The above disclosure generally describes the present invention. A more complete understanding can be obtained by reference to the following specific examples. These examples are described solely for the purpose of illustration and are not intended to limit the scope of the invention. Changes in form and substitution of equivalents are contemplated as circumstances might suggest or render expedient. Although specific terms have been employed herein, such terms are intended in a descriptive sense and not for purposes of limitation.

The following non-limiting examples are illustrative of the present invention:

EXAMPLES

Example 1

Centromere Positions in Nuclei of Normal, Immortalized, and Malignant B Cells

The three-dimensional (3D) positions of centromeres have been studied in several cell systems. However, data on centromere positions during cellular transformation remain elusive. This study has focused on B lineage cells and investigated the centromere positions in primary, immortalized and tumor cells.

Using CentroView™, a program the inventors developed to measure nuclear centromere positions, the positions of centromeres in primary, immortalized and malignant mouse B cells were determined. The results show that centromeres exhibit altered nuclear positions in immortalized and malignant B cells. These changes are independent of previously described cell cycle-dependent centromere dynamics.

In summary, the inventors have shown that the 3D positions of centromeres are altered during cellular transformation. These nuclear changes reflect structural remodeling of mammalian nuclei during oncogenesis and may impact on the structural organization of chromosomes.

Methods

Cells

Immortalized diploid mouse PreB lymphocytes were grown in RPMI 1640 media with 10% fetal bovine serum (FBS), 1% L-glutamine, 1% sodium-pyruvate, 1% penicillin-streptomycin, and 0.1% β-mercaptoethanol (Invitrogen/Gibco, Burlington, ON, Canada) at 37° C. in a humidified atmosphere and 5% $CO_2$. Cells were maintained at $10^5$ to $10^6$ cells/ml. Three-dimensional (3D) fixation [Chuang T C, Moshir S, Garini Y, Chuang A Y, Young I T, Vermolen B, van den Doel R, Mougey V, Perrin M, Braun M, Kerr P D, Fest T, Boukamp P, Mai S: The three-dimensional organization of telomeres in the nucleus of mammalian cells. (2004) *BMC Biol,* 3:2-12] was used to maintain and preserve the structure of the cells.

For G1/S synchronization, PreB cells were incubated for 42 hours in RPMI 1640 (Gibco, Burlington, ON, Canada) that had been depleted of the amino acids methionine, cysteine, and L-glutamine. Cells were returned to complete RPMI 1640 media (Gibco, Burlington, ON, Canada) with mimosine at a concentration of 0.4 µg/ml for 8 hours [Kuschak T I, Kuschak B C, Taylor C L, Wright J A, Wiener F, Mai S: c-Myc initiates illegitimate replication of the ribonucleotide reductase R2 gene. (2002) *Oncogene,* 21:909-920] and were subsequently 3D fixed. For G2/M synchronization, PreB cells were incubated for 8 hours in RPMI 1640 (Gibco, Burlington, ON, Canada) with nocodazole (Sigma-Aldrich, Oakville, ON, Canada) at a concentration of 1 µg/ml and 3D fixed.

The plasmascytoma cell line MOPC460D was grown in RPMI 1640 with 10% FBS, 1% L-glutamine, 1% sodium-pyruvate, 1% penicillin-streptomycin, (all the above reagents were from Invitrogen/Gibco, Burlington, ON, Canada) and 100 µl of Interleukin 6 (IL6) per 10 ml plate at 37° C. in a humidified atmosphere and 5% $CO_2$. 3D fixation was done when they became confluent. The MOPC460D cell line was a gift from Dr. Mushinski (NIH, USA). Primary splenic lymphocytes were extracted from T38HxBalb/c mice (Central Animal Care protocol number 02-039/1/2/3) and 3D fixed.

Cell Cycle Profiles

A cell cycle profile was done on immortalized PreB lymphocyte cells. Cells were analyzed according to their DNA content for the determination of G1 and/or G2 phase is performed as described by [Caporali A, Wark L, Vermolen B J, Garini, Y., Mai S: Telomeric aggregates and end-to-end chromosomal fusions require my box II. (2006) *Oncogene,* In press]. Cell synchronization was done as described [Caporali A et al. (2006)]. Flow analysis was carried out using an EPICS Altra cytometer (Beckman-Coulter, Mississauga, ON, Canada).

Centromere FISH

Three-dimensional (3D) fixation was performed on immortalized PreB (non-synchronized, G1- and G2-synchronized), MOPC460D, and normal spleen cells from specific pathogen-free (SPF) mice, T38HxBalb/c. The 3D fixed cells were laid onto slides. For centromere hybridizations, they were incubated with RNAase A (100 µg/ml) for 1 hour in a humidified 37° C. incubator. The slides were then incubated in 50 µg/ml pepsin treatment in 0.01N HCl at 37° C. for 10 minutes. The slides then went through dehydration steps of 70%, 90% and 100% ethanol, air dried and then denatured in 70% formamide/2×SSC for 2 minutes at 70° C. 7 µl (per slide) of the Pan Centromeric Probe (Cedarlane, Cambio, UK) was denatured at 90° C. for 5 minutes, then placed on ice for 5-10 minutes. Probe, cover slips were applied and sealed with rubber cement. The slides were placed in a 37° C. humidified incubator and left overnight. Post-hybridization washes were 3 washes of 50% formamide/2×SSC at 45° C. for 5 minutes each. Slides were then rinsed in and washed in 4×SSC/0.1% Tween 20 wash at 45° C. for 5 minutes. Excess fluid was drained off and 20 µl of 1 µg/ml DAPI was applied, then one drop of vectashield (Vector Laboratories, Burlington, ON, Canada) was added. Slides were imaged right away as described in '3D Image Acquisition'. Telomere FISH was performed as described [Louis S F et al. (2005)]. Three independent experiments were performed.

3D Image Acquisition

Image acquisition was performed on 147 nuclei per cell line and/or cell cycle phase using an Axioplan 2 microscope (Carl Zeiss Inc. Canada) and an AxioCam HR CCD (Carl Zeiss Inc. Canada). A 63x/1.4 oil objective (Carl Zeiss Inc. Canada) was used and an acquisition time of 300 ms for FITC and 20-50 ms for DAPI. Eighty-to-ninety z-stacks were acquired at a resolution of xy: 107 nm and z: 200 nm for each stack. The Axiovision 3.1 software (Carl Zeiss Inc. Canada) and the constrained iterative algorithm [Schaefer L H et al. (2001)] were used for the deconvolution.

3D Segmentation and Analysis Used in CentroView

Segmentation of distinct centromeric DNA regions and analysis of their nuclear positions was performed using a new software tool that we have called CentroView. CentroView runs under the Matlab environment and was developed using the Matlab Graphical User Interface Development Environment (GUIDE) (The MathWorks, Natick, Mass., USA). The DIPLib image-processing library is used to support much of the functionality of CentroView, and is available as public domain software at <http://www.qi.tnw.tudelft.nl/DIPlib/>.

CentroView loads a three-dimensional input image consisting of separate channels for the FITC-labeled centromeric DNA and the DAPI-counterstained nucleus. It performs segmentation of the distinct centromeric regions on the FITC channel image using a unique approach based on the Isodata thresholding algorithm [Ridler T W and Calvard S: Picture thresholding using an iterative selection method. (1978) *IEEE Trans. on Systems, Man, and Cybernetics,* SMC-8(8): 630-632]. The segmented image is then used in combination with the DAPI nuclear image to quantify the distance of each centromeric region with respect to the nuclear center.

Segmentation Used in CentroView

The maximum projections of a typical 3D FITC-channel centromere image onto each of the three major optical planes illustrate a large difference between the background intensity levels and the intensities of the centromeric regions, lending to the usage of a threshold to segment the centromeric region from background. CentroView employs the Isodata algorithm as developed by Ridler and Calvard [Ridler and Calvard (1978)] to automatically determine the optimal threshold level. All quantification of total intensity of centromeric DNA is done on the Isodata thresholded image.

Figure 3:
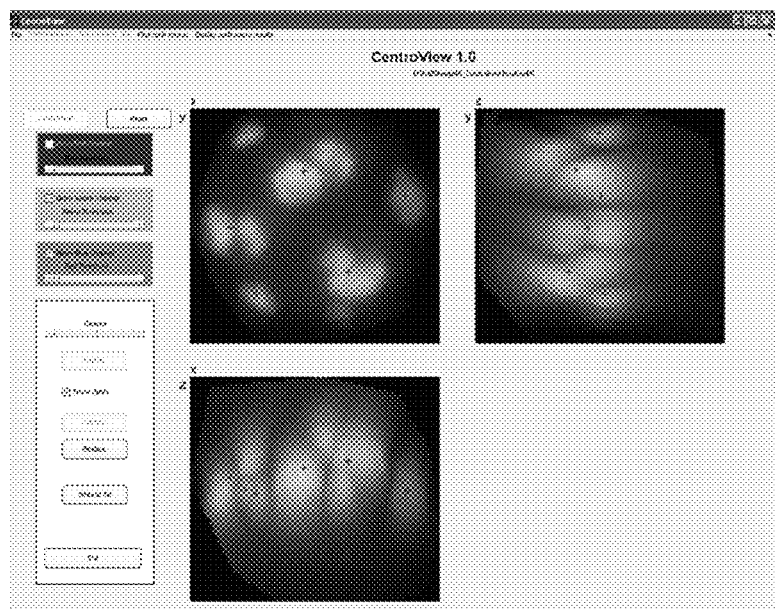
FIG. 3 is an overview of CentroView™. Panel a) Screen shot using 2.5 threshold level. Panel b). Screen shot using 3.2 threshold level. The 3.2 threshold is more accurate when measuring the position of two centromeres that are close together which may be mistaken for one centromere. Panel c). The segmentation algorithm at work. Panel c) (a) One region from the binary image produced by thresholding the FITC channel image at the Isodata threshold. Quantitative observation of intensity and region size is performed on the original image based on the area indicated by this binary image. Panel c) (b) Three distinct regions are observed by thresholding the image at some higher threshold. This threshold is adjusted until the region separation observed is verified by the user as being consistent with the maximum projection images. Panel c) (c) The quantitative information regarding intensity and size gathered from a) is proportionately distributed over the distinct regions observed in b). Panel d) (a) CentroView begins the analysis of nuclear position by calculating the Euclidean distances between the nuclear center and the center of mass of each centromeric region. Panel d) (b) A radial arm is then projected in the direction of each region's center of mass, extending from the nuclear center to the nuclear boundary. The parameter $d_c$ is then calculated by expressing each of the Euclidean distances found in Panel d) (a) in terms of its corresponding radial arm in Panel d) (b).
Figure 3:
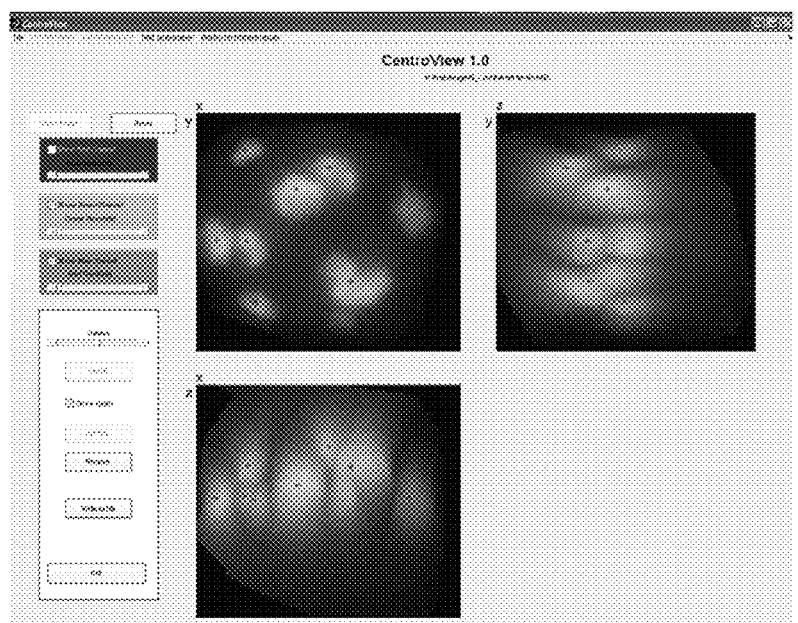
Figure 3:
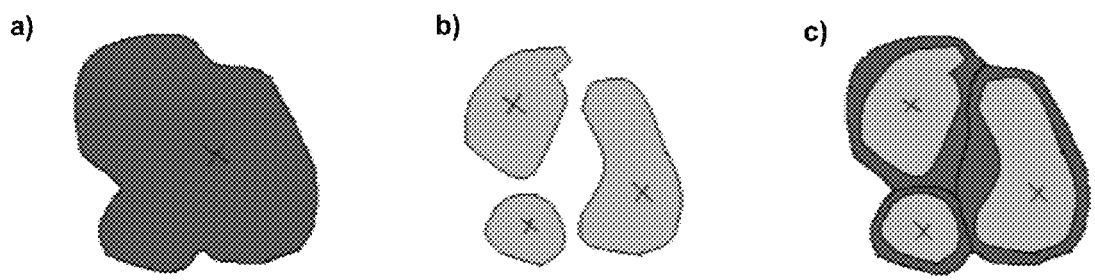
Figure 3:
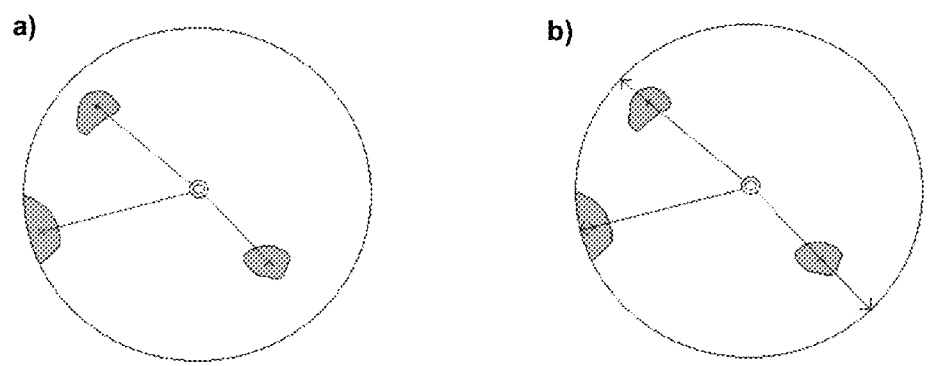
Figure 4A:
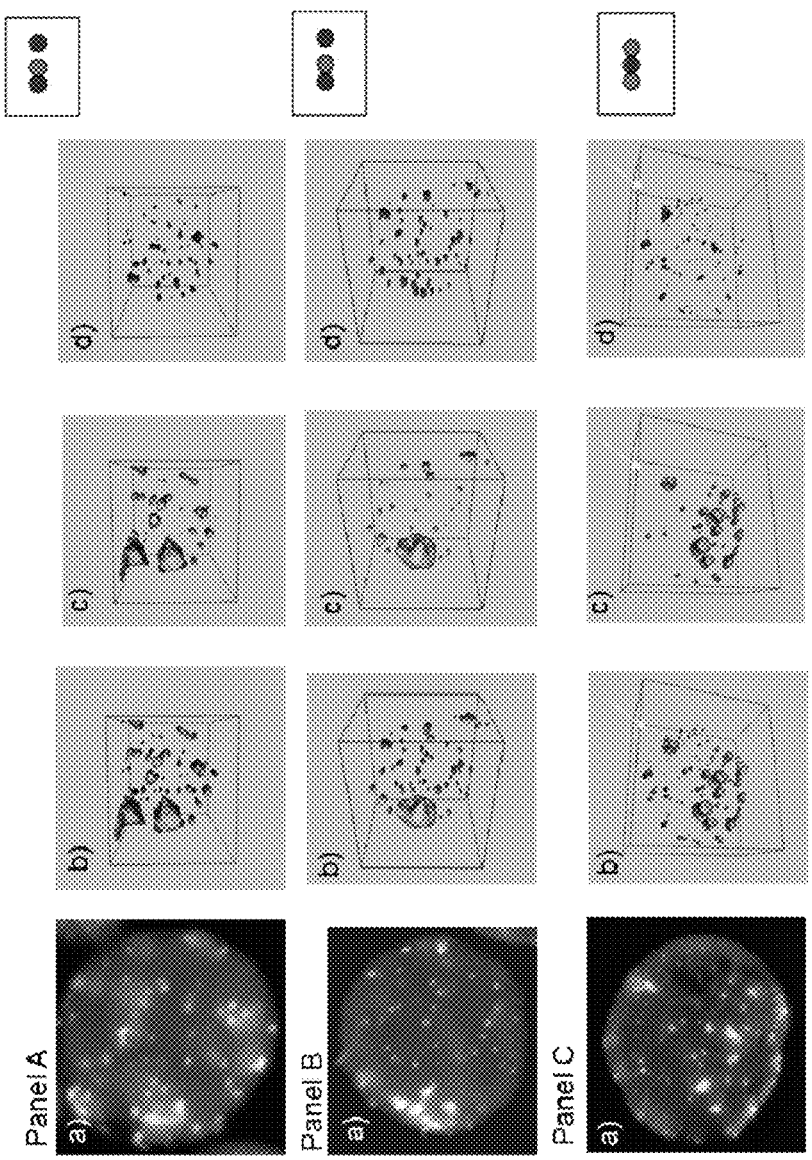
FIG. 4 shows nuclear centromere and telomere distribution patterns. Representative images of dual color hybridization of B lineage cells with a centromere probe (green) and a telomere probe (red) on interphase nuclei (blue). Panels A-F represent different B cell nuclei as follows, Panel A: Primary lymphocyte nucleus of T38HxBalb/c; Panel B: nucleus of PreB cell, Panel C: nucleus of MOPC460D; Panel D: PreB cell nucleus without MycER™-activation, 30 hours after mock treatment with ethanol [Louis S F, Vermolen B J, Garini Y, Young I T, Guffei A, Lichtensztejn Z, Kuttler F, Chuang T C, Moshir S, Mougey V, Chuang A Y, Kerr P D, Fest T, Boukamp P, Mai S. (2005) *Proc Natl Acad Sci USA*, 102: 9613-9618]; Panel E: PreB cell nucleus 30 hours after MycER™-activation; Panel F: Ba/F3 cell nucleus without Δ106-MycER™-activation, 30 hours after mock treatment with ethanol; Panel G: Ba/F3 cell nucleus 30 hours after Δ106-MycER™-activation. Each panel illustrates a nucleus in 2D (Panels A-G (a)) and in 3D (Panels A-G (b-d)). Of the 3D panels, b) represents the dual color hybridization with centromeres in green and telomeres in red, c) illustrates the centromeric signals only, and d) shows the telomeric hybridization signals. Yellow arrows point to co-localizations of centromere-telomere-centromere (CTC) hybridization signals (green-red-green). Telomere-centromere hybridization signals are also highlighted in small cartoons on the right side of each panel.
Figure 4B:
Figure 4B:
Figure 4B:
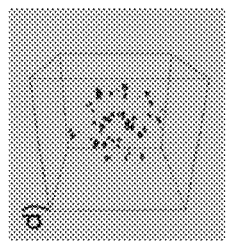
Figure 4B:
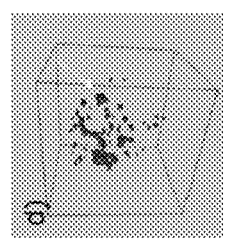
Figure 4B:
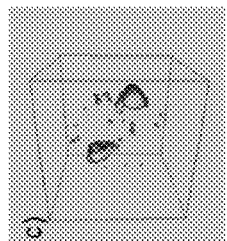
Figure 4B:
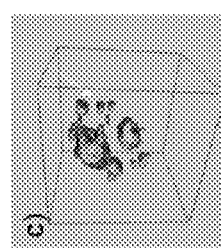
Figure 4B:
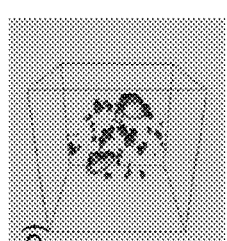
Figure 4B:
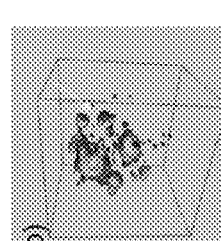
Figure 4B:
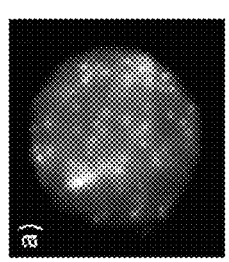
Figure 4B:
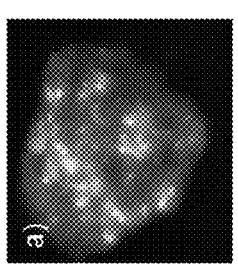
Figure 4C:
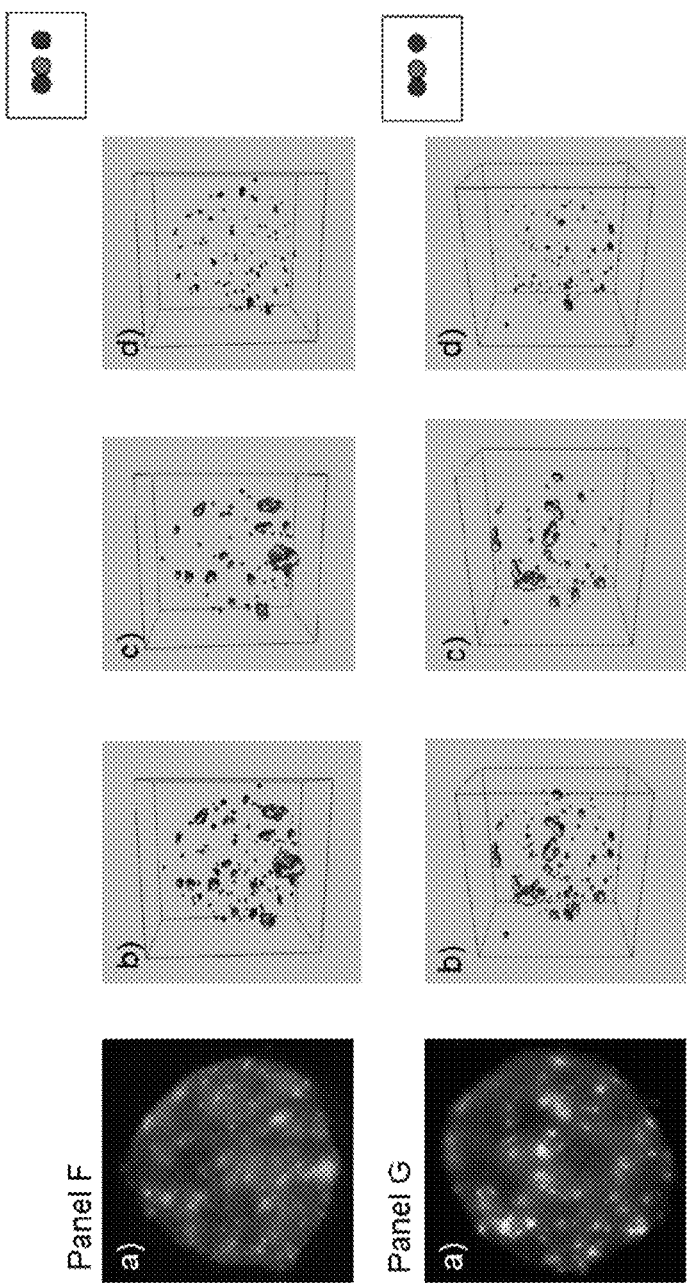

Some of effects of convolution are present even after the processing of the 3D images using the constrained iterative deconvolution method. Centromeric regions are out of focus in image slices at certain depths in the 3D nucleus, which results in the intensity of the pixels surrounding actual regions to be at intensity levels higher than that of the Isodata threshold. The artificially elevated intensity levels of the surrounding pixels are caused by the blurring effect that centromeric regions experience at out-of-focus depths, and when two or more of such regions are in close proximity of one another, the overlap of surrounding pixels from multiple regions causes them to appear connected. To overcome this misclassification problem, CentroView uses a second threshold to segment closely spaced regions from one another. The second threshold is a user given parameter expressed as some multiple of the Isodata threshold level (typically 2.5). FIG. 3 (panel a and b) illustrates the effect of varying threshold values.

This technique is effective at region separation since the artificially elevated intensities of the surrounding pixels are generally lower than those of the actual centromeric regions. Once the regions have been separated at the higher threshold, any group of regions that appeared connected in the Isodata thresholded image are assigned total intensities proportionately based upon the total intensity of the single connected region. CentroView thus allows for accurate region separation through user-assisted computer vision without introducing any bias into the quantification of region intensities. FIG. 3 (panel c) demonstrates the segmentation algorithm.

Analysis Used in CentroView.

CentroView computes the center of mass, ($x_c$, $y_c$, $z_c$), of each segmented region using position coordinates in three-dimensional space weighted by the intensity of each corresponding voxel, as follows:

$$x_c = \frac{\sum_i^N I_i x_i}{\sum_i^N I_i}$$

$$y_c = \frac{\sum_i^N I_i y_i}{\sum_i^N I_i}$$

$$z_c = \frac{\sum_i^N I_i z_i}{\sum_i^N I_i}$$

where li is the intensity of voxel i, N is the total number of all voxels in the region, and x, y and z are all voxel coordinates. This center of mass value is used an approximation of the position of the centromeric region. The DAPI channel image is then thresholded using the Isodata algorithm to produce a binary image of the nucleus, and the center of the mass of the nucleus is calculated in the same way as for the centromeric regions. To determine the position of each region within the nucleus, the Euclidean distance between the center of mass of the region and the nuclear center is computer. A radial arm is then projected from the nuclear center towards the nuclear boundary in the direction of the centromeric region. The distance between the region and the nuclear center is fractionally expressed in terms of the measured distance of this radial arm, with 0% being at the nuclear center and 100% being the nuclear boundary. This percentile position metric is the output of the nuclear position analysis, and is denoted dc. (FIG. 3, panel d) illustrates the computation of $d_c$. It should be noted that since thresholding is applied separately to the FITC and DAPI channels, minor variability between the determined nuclear boundary and centromeric locations can sometimes result in dc values slightly greater than 100%. For dc values within a 5% error margin, the centromeric region can generally be interpreted as being within the nuclear periphery, while values with greater error margins are usually the result of extra-nuclear debris or centromeric regions from neighboring nuclei.

Statistical Analysis

Primary lymphocytes of T38HxBalb/c mice were used as controls throughout this study and were compared to the MOPC460D and the immortalized PreB cells. The immortalized PreB cells were used as a control when compared to the immortalized PreB G1 and the immortalized G2. Overall significance of centromere distribution throughout the nucleus was analyzed using the distribution at 0-20%, 20-40%, 40-60%, 60-80%, 80-100%, and >100% (<150%) regions from the centre of the nucleus. The Kruskal-Wallis test was used for analysis for all the comparisons.

List of abbreviations. 3D: three-dimensional, 2D: two-dimensional.

Results and Discussion

The 3D Organization of Centromeres is Significantly Altered in Interphase Nuclei of Immortalized and Tumor Cells The 3D organization of the nucleus is a direct reflection of its stability [Zink D et al. (2004); Louis S F et al. (2005)]. To examine the 3D organization of centromeres, images of nuclear centromere distribution were acquired in mouse primary lymphocytes (from T38HxBALB/c mice), diploid immortalized PreB cells [Mai S, Hanley-Hyde J, Rainey G J, Kuschak T I, Paul J T, Littlewood T D, Mischak H, Stevens L M, Henderson D W, Mushinski J F: Chromosomal and extra-chromosomal instability of the cyclin D2 gene is induced by Myc overexpression. (1999) *Neoplasia*, 1:241-252; Louis S F et al. (2005)], and mouse plasmascytoma cells (MOPC460D) (Methods; FIG. 1, Panel A). As shown in representative images in two and three dimensional illustrations, the distribution of centromeres (green) in nuclei (blue) of primary B cells and of immortalized PreB cells is primarily peripheral (FIG. 1, Panel A, (a,b) and (c,d) respectively). In contrast to this, MOPC460D cells exhibit a tendency towards a more central centromeric distribution (FIG. 1, Panel A, e and f).

These findings on the peripheral position of centromeres in primary lymphocytes are in agreement with an earlier study by Weierich et al. [Weierich C, Brero A, Stein S, von Hase J, Cremer C, Cremer T, Solovei I: Three-dimensional arrangements of centromeres and telomeres in nuclei of human and murine lymphocytes. (2003) *Chromosome Res*, 11:485-502] who analyzed human and mouse lymphocytes in G0 as well as human skin fibroblasts. The authors found no internal centromeres in about 60% of the nuclei. Forty percent contained 1-2 internal signals. The distribution of the centromere clusters showed a maximum at the relative radius of 88-90%. Eighty percent of all centromeres were located in the immediate proximity of the nuclear border.

In this study, the exact centromeric distribution in mouse B cell nuclei was determined along a radial axis from the centre of the nucleus to the nuclear periphery (FIG. 1, Panel B). The centromeric distribution was defined in percentage increments from 0-100, with 0% being the nuclear centre and 100% being the nuclear edge using the CentroView software that was developed for this purpose (Methods).

The overall distribution of centromeres along the radial nuclear axis was significantly different when centromere distributions of primary lymphocytes were compared with those of immortalized PreB or MOPC460D cells ($p<0.0001$) (FIG. 1, Panel B (a and c)). MOPC460D cells had the highest frequencies of centromeres within the nuclear radial space of 0-60% (FIG. 1, Panel A (e and f); FIG. 1, Panel B (c)). The overall centromere distribution of PreB cells along the radial axis was also not only significantly different from that of primary lymphocytes (p<0.0001) (FIG. 1, Panel A (a-d); FIG. 1, Panel B (a and b)), but also significantly altered from that of MOPC460D cells (p=0.007) (FIG. 1, Panel B (b and c)). PreB cells exhibited higher frequencies of centromeres in the 20-60% range than primary lymphocytes with a predominantly peripheral centromere distribution. In addition, they did not display a central centromeric organization and this made them significantly different from MOPC cells.

In conclusion, the nuclear distribution of centromeres is significantly different in primary, immortalized and tumor cells.

Cell Cycle-Dependent Nuclear Centromere Distribution

Centromere positions of a wide range of human nuclei including non-cycling (G0) peripheral lymphocytes, terminally differentiated monocytes, cycling phytohemagglutinin-stimulated lymphocytes, diploid lymphoblastoid cells, primary fibroblasts, and neuroblastoma cells (SH-EP) display a cell cycle-dependent centromere organization [Solovei I et al. (2004)] Solovei and co-workers [Solovei I et al. (2004)] showed that centromeres shift to the nuclear periphery in late G1 and early S. A peripheral localization of centromeres was most pronounced in non-cycling (G0) cells. In these cells, centromeres formed clusters at the periphery. In late S and G2, centromeres partially decluster and are observed in the nuclear interior [Solovei I et al. (2004)].

Figure 2:
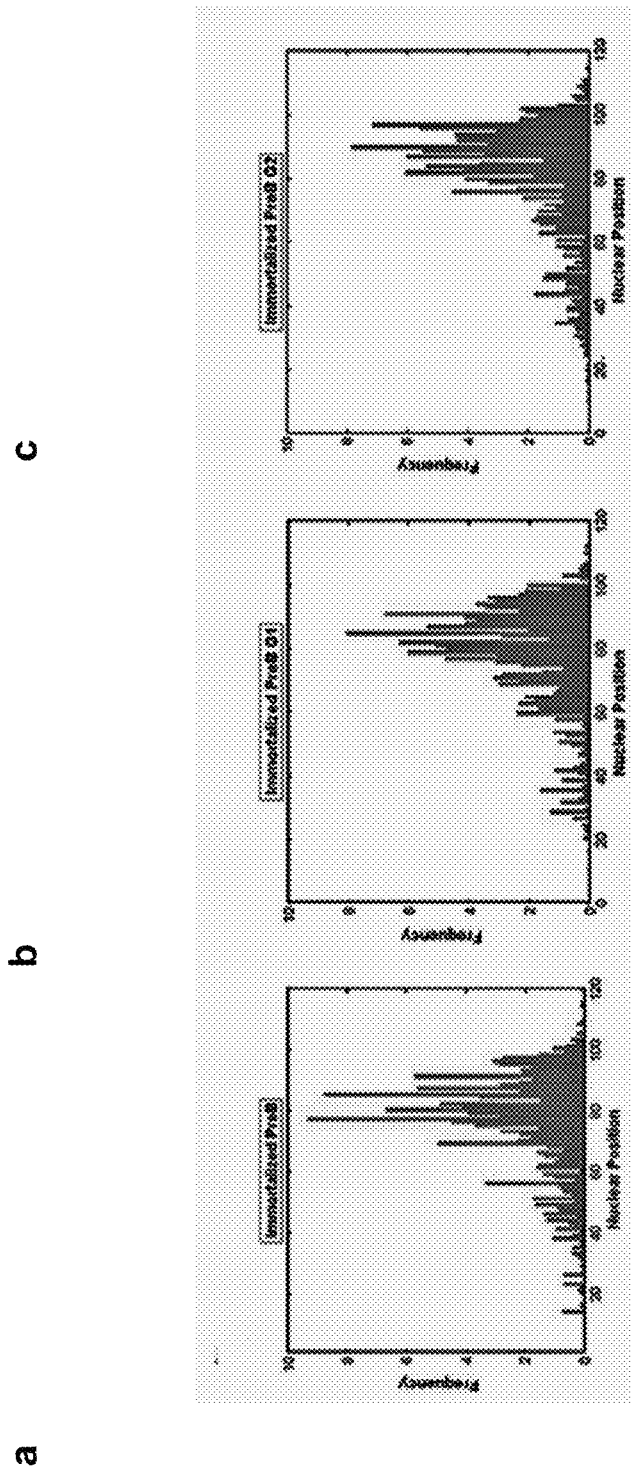
FIG. 2 shows frequencies of centromere distribution during the cell cycle. PreB cells were synchronized and nuclei were analyzed as described in Methods. The graphs show the frequencies of centromere distributions along the radial axis (nuclear positions 0-100) for nuclei of non-synchronized cells (a), of G1-arrested cells (b), and of G2 arrested cells (c).

Since the data summarized above (FIG. 1) illustrated centromere distribution frequencies in nuclei of MOPC460D and immortalized PreB cells that were cycling cells, while those of primary lymphocytes from specific pathogen-free mice were resting lymphocytes (G0/G1 phase), the impact of the cell cycle on the nuclear positions of centromeres was evaluated. To this end, cell cycle profiles of non-synchronized, and G1- or G2-synchronized immortalized PreB cells were obtained using the following fluorescent activated cell sorter (FACS) [Caporali A et al. (2006)]. Parallel cell samples of the identical experiments were 3D fixed and the nuclear centromeric distributions were examined after 3D imaging with CentroView (FIG. 2). The data indicates that non-synchronized PreB cells show lower frequencies of centromeres at the nuclear periphery and edge than PreB cells in G1 or G2 (FIG. 2a-c, p<0.0001). There was no significant difference in centromere distribution between G1 to G2 cells (FIG. 2b,c; p=0.5247). In conclusion, the nuclear centromeric positions of PreB cells are cell cycle dependent. Importantly, at none of the investigated time points did nuclear centromere positions in PreB cells appear similar to those found in MOPC460D or primary mouse lymphocytes (FIG. 1). Thus, the differences in nuclear centromere distribution that we noted between primary lymphocytes, immortalized PreB cells, and MOPC460D cells are independent of cell cycle phases and illustrate alterations in nuclear centromere organization.

Conclusions

Using CentroView, the inventors have measured the nuclear distribution patterns of centromeres in mouse B lineage cells. The inventors found significant differences in the nuclear distribution of centromeres between normal, immortalized and tumor cells. More centromeres were found in the centre and throughout the nucleus in mouse plasmacytoma (MOPC460D) cells than in primary mouse lymphocytes or immortalized PreB cells that display a mainly peripheral 3D centromeric order. The centromeric distribution in immortalized PreB cells compared to the primary lymphocytes showed a similar nuclear distribution in the peripheral range of 80 to 100%. However, immortalized PreB cells displayed a significantly different centromeric distribution within the radial range of 20 to 60%. Without being limited to theory, the inventors hypothesize that these differences in centromeric distribution frequencies reflect an altered nuclear organization during cellular transformation with potential impact on genome stability.

Example 2

Mouse Robertsonian Chromosome Formation Following c-Myc Deregulation

Robertsonian (Rb) chromosomes occur in human and murine cancers. Mechanisms involved in their generation remain elusive. The inventors here report on a novel mechanism of c-Myc oncogene-mediated Rb chromosome formation. The results show that Rb chromosomes are generated during nuclear remodeling of centromere positions in mouse interphase nuclei in a c-Myc oncogene- and myc boxII-dependent manner via telomere fusions at centromeric termini of acrocentric chromosomes.

Materials and Methods

Abbreviations

Q-FISH: quantitative fluorescent in situ hybridization; SKY: spectral karyotyping; Rb chromosomes: Robertsonian chromosome; 3D: three-dimensional; 2D: two-dimensional; BBF: breakage-bridge-fusion; TCT: telomere-centromere-telomere; CTC: centromere-telomere-centromere.

Cells

All cells used are listed in Table 1. Primary splenic lymphocytes and primary plasmacytoma (PCT1G1) were directly isolated without any in vitro cultivation from T38HxBalb/c mice (Central Animal Care protocol number 02-039/1/2/3). PreB lymphocytes [Mai S et al. (1999); Louis S F et al. (2005)] were grown in RPMI 1640 media with 10% fetal bovine serum (FBS), 1% L-glutamine, 1% sodium-pyruvate, 1% penicillin-streptomycin, and 0.1% β-mercaptoethanol (Invitrogen/Gibco, Burlington, ON, Canada) at 37° C. in a humidified atmosphere and 5% $CO_2$. Cells were maintained at $10^5$ to $10^6$ cells/ml. The plasmascytoma cell line MOPC460D (a gift from Dr. J F Mushinski (NIH, USA)) was grown in RPMI 1640 with 10% FBS, 1% L-glutamine, 1% sodium-pyruvate, 1% penicillin-streptomycin, (all the above reagents were from Invitrogen/Gibco, Burlington, ON, Canada) and 100 μl of interleukin 6 (IL6) per 10 ml plate at 37° C. in a humidified atmosphere and 5% $CO_2$. Ba/F3 cells [Fest T, Mougey V, Dalstein V, Hagerty M, Milette D, Silva S, Mai S. (2002) Oncogene 21:2981-2990; Fest T et al. (2005)] with Δ106-MycER™ were grown in RPMI 1640 (Invitrogen, Burlington ON, Canada), containing 10% fetal bovine serum (Gibco, Burlington ON, Canada), 1% WEHI supernatant (IL3), and 0.021% of plasmocin (Cayla, Toulouse, France). Cells were grown and maintained at a density of $10^5$ to $10^6$ cells/ml. MycER™ in PreB cells and Δ106-MycER™ in Ba/F3 cells was activated by 4-hydroxytamoxifen (4HT) (Sigma-Aldrich, Oakville ON, Canada) at a final concentration of 100 nM in $10^5$ cells/ml. Cells were split 24 hours prior induction. Three-dimensional (3D) fixation [Chuang T C et al. (2004)] was used to maintain and preserve the structure of the cells.

Peptide-Nucleic-Acid (PNA)-Fish with Centromeres and Telomeres

PNA-FISH was performed on both 3D interphase and 2D metaphases samples derived from the above cells. The PNA human centromeric probe (Applied Biosystems, Foster City, Calif., USA) was custom-made to the sequences listed below. It hybridized to all mouse centromeres (FIG. 6).

PNA centromere probe sequences used in this study:

```
Sequence 1   (N-Terminus)Flu-OEE-ATTCGTTGGAAACGGGA-
             EE(C-Terminus)

Sequence 2   (N-Terminus)Flu-OEE-CACAAAGAAGTTTCTGAG-
             EE(C-Terminus)

Sequence 3   (N-Terminus)Flu-OEE-CAGACAGAAGCATTCTCA-
             EE(C-Terminus)

Sequence 4   (N-Terminus)Flu-OEE-TGCATTCAACTCACAGAG-
             EE(C-Terminus).
```

The PNA telomeric probe was purchased from DAKO (Glostrup, Denmark). 3D fixed interphase nuclei were fixed onto the slide using a 3.7% Formaldehyde/PBS [Mai S et al. (1999)]. The PNA human centromeric probe was denatured at 80° C. for 5 minutes and then added to the slide in conjunction with the PNA telomeric probe. The slides were denatured at 80° C. for 3 minutes, and subsequently hybridized for 2 hours at 30° C. in using the Hybrite™ system, and then washed in 70% formamide/2×SSC. 0.2 µg/ml DAPI was applied, and finally one drop of vectashield (Vector Laboratories, Burlington, ON, Canada) was added. All slides were imaged right away to avoid uneven imaging conditions and were handled as described in '3D Image Acquisition'.

3D Image Acquisition

Image acquisition was performed on 30 interphase nuclei per cell line using an Axioplan 2 microscope (Carl Zeiss Inc. Canada) and an AxioCam HR CCD (Carl Zeiss Inc. Canada). A 63x/1.4 oil objective (Carl Zeiss Inc. Canada) was used and an acquisition time of 300 ms for FITC (centromere), 200 ms for Cy3 (telomere) and 20-50 ms for DAPI (nuclei). Eighty-to-ninety z-stacks were acquired at a resolution of xy: 107 nm and z: 200 nm for each stack. The Axiovision 3.1 software (Carl Zeiss Inc. Canada) and constrained iterative algorithm [Schaefer L H et al. (2001)] were used for deconvolution.

Scoring of Centromere-Telomere Signals in 3D Nuclei

Centromere-telomere hybridization signals were scored as follows: in nuclei with declustered centromeres, telomere signals that flanked centromeres from one or two sides were counted as normal. In contrast, when telomere signals were flanked by centromere signals on two sides, such signals were scored as aberrant. Telomere-centromere-telomere signals (TCTs) thus represent the normal nuclear organization, while centromere-telomere-centromere signals (CTCs) represent an aberrant nuclear organization. Nuclear domains with clustered centromeres were not included in this analysis. Note that telomeric signals at a distance of <200 nm are detected as one signal [Chuang T C et al. (2004)].

Spectral Karyotyping (SKY) Analysis

SKY was performed using the ASI (Applied Spectral Imaging, Vista, Calif., USA) kit for mouse and the supplier's hybridization protocols. The Spectra Cube™ (ASI) on a Carl Zeiss Axioplan 2 microscope was used using a X63 oil objective and the Case Data Manager 4.0 software (ASI) for PC to carry out analyses. A minimum of 20 metaphases were examined for PreB induced and non-induced, MOPC460D, T38HxBalb/c, and Δ106 induced and non-induced. Metaphases were then analyzed for Rb fusions, and matching control time points were statistically compared using the Fisher's exact test. p values of less then 0.05 were considered significant.

Results

Myc and myc boxII-Dependent Nuclear Remodeling of Centromere Positions

Figure 5A:
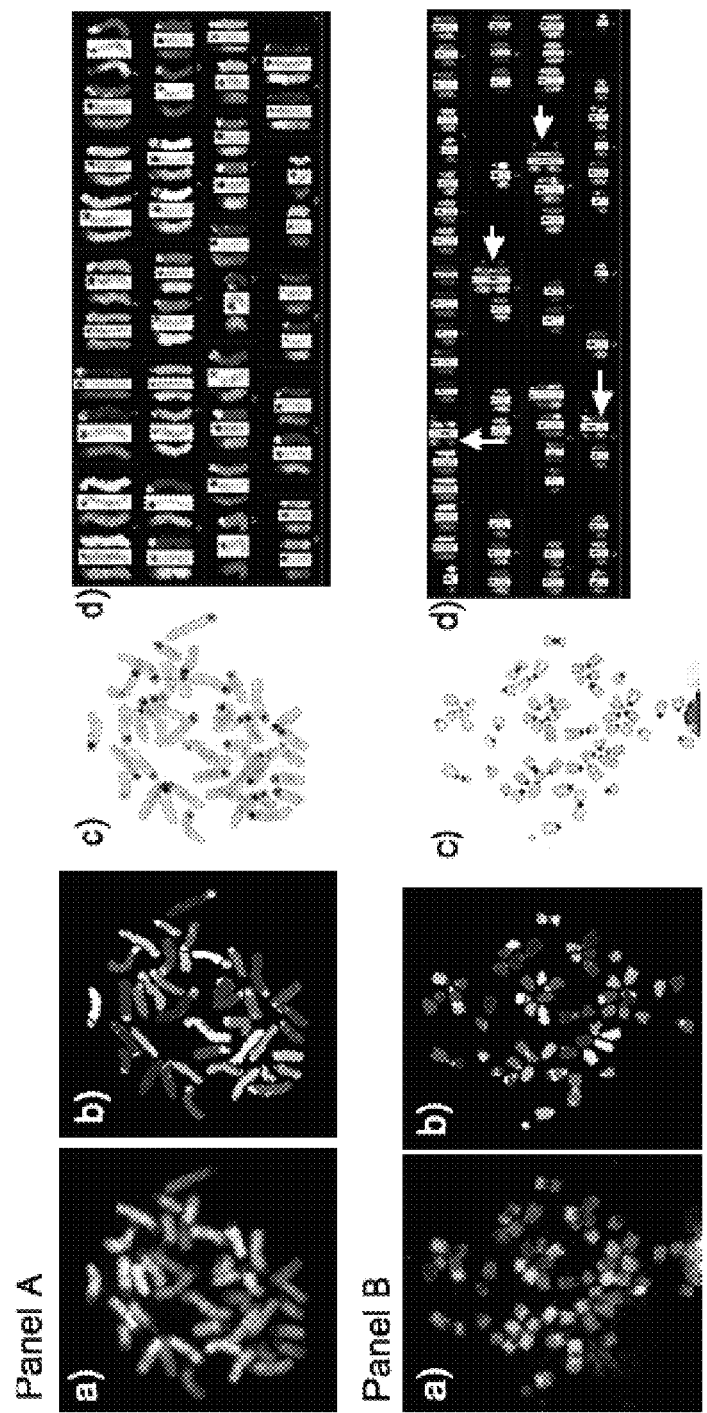
FIG. 5 is a spectral karyotyping (SKY) of metaphases derived from B lineage cells of this study. Representative images from SKY analyses are shown as follows: Panel A: primary lymphocytes from T38HxBalb/c mice, Panel B: MOPC460D, Panel C and D: Pre B cells in the absence (C) or presence (D) of MycER™-activation; Panels E and F: Ba/F3 Δ106-MycER™ without (E) or with (F) Δ106-MycER™-activation. Arrows point to Rb fusion chromosomes. The Rb(8;8) in Ba/F3 cells is constitutional and has been noted previously [Fest T, Guffei A, Williams G, Silva S, Mai S. (2005) *Oncogene*, 24:2944-2953].
Figure 5B:
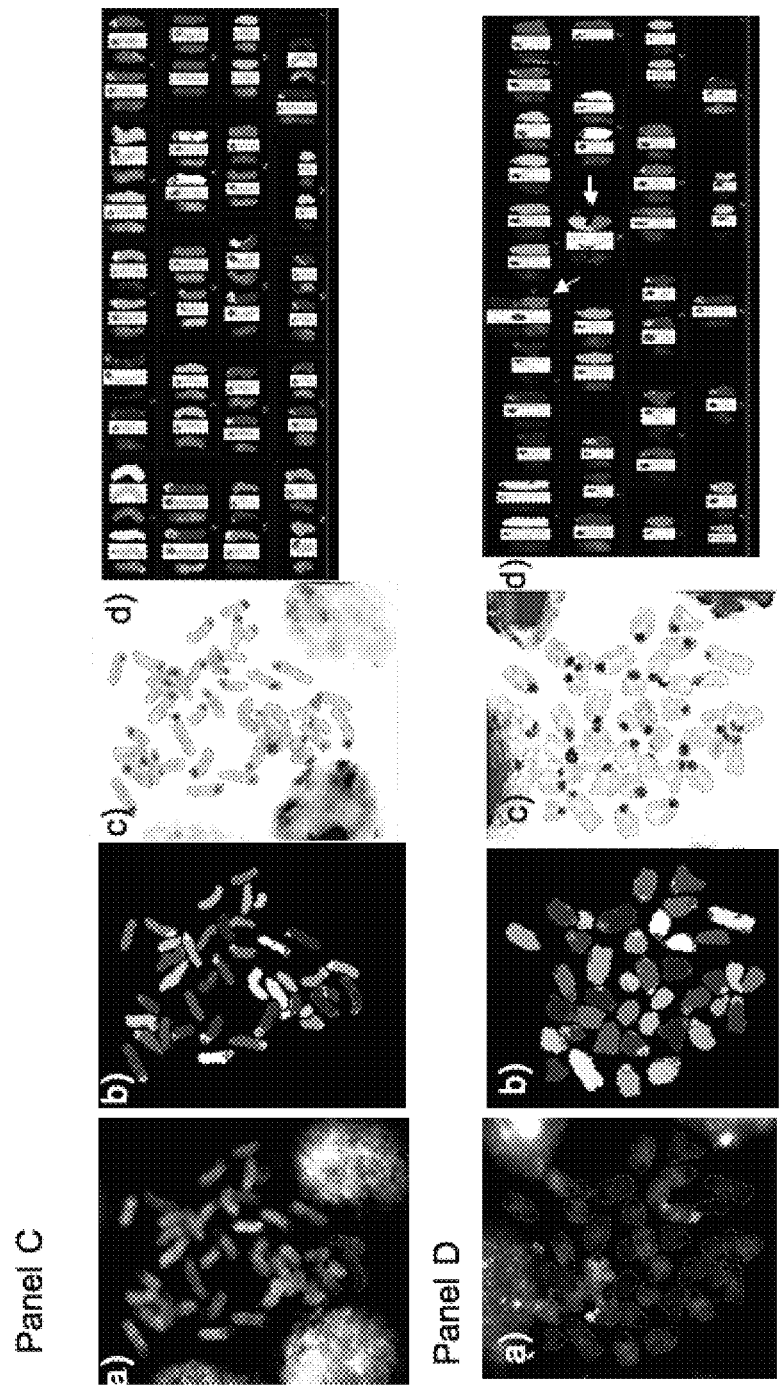
Figure 5C:
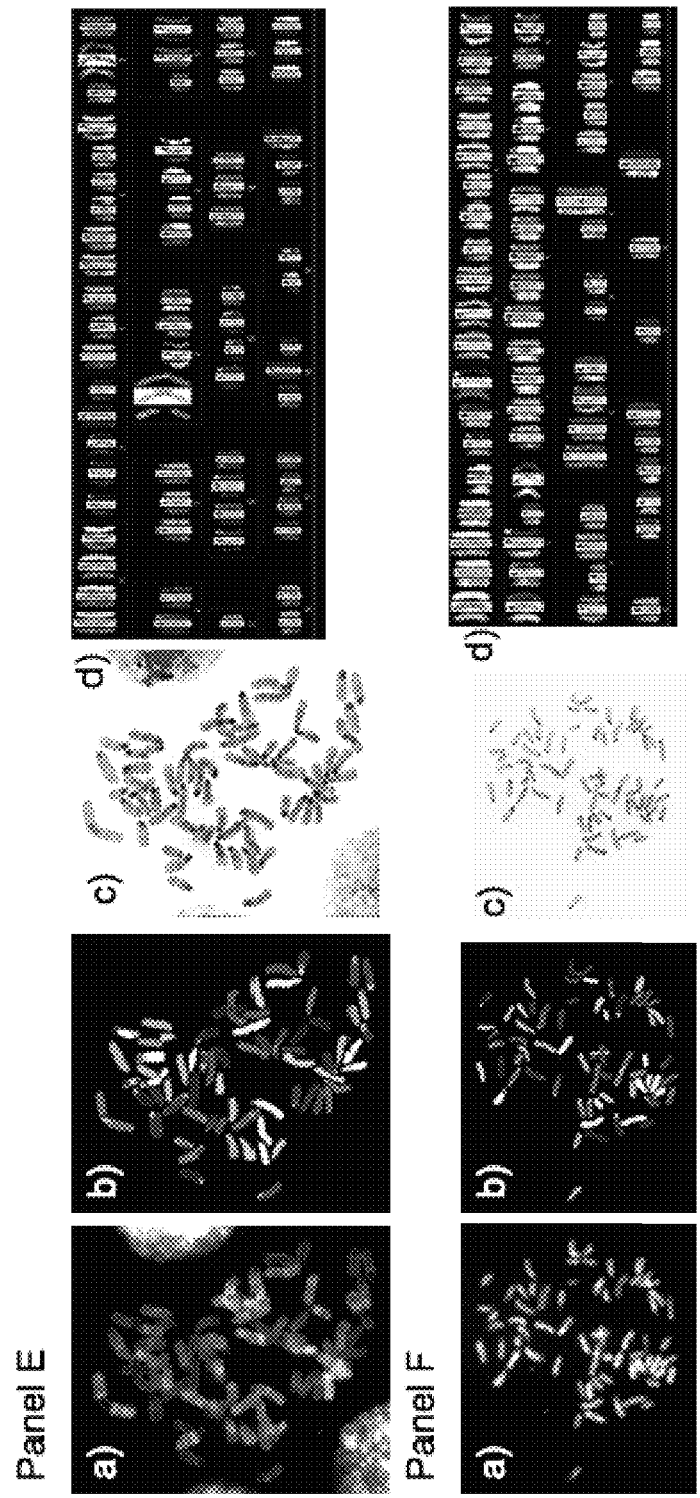
Figure 6A:
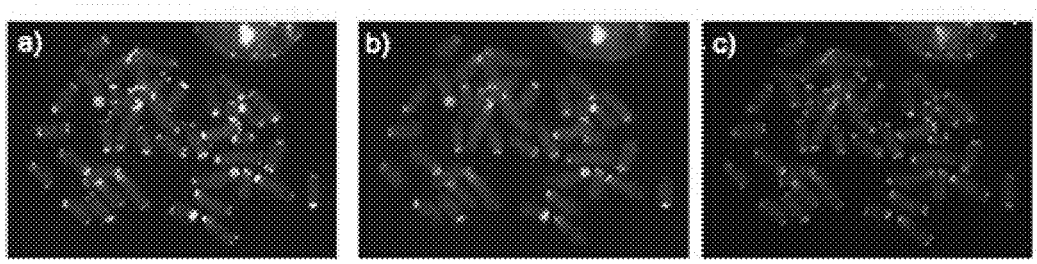
FIG. 6 shows images of centromere-telomere FISH performed on metaphases of B lineage cells. Representative images are shown from the following cells: Panel A: primary lymphocyte metaphase from a T38HxBalb/c mouse; Panel B: metaphase of MOPC460D; Panel C: partial metaphase of the primary mouse plasmacytoma PCT1G1; Panel D: PreB cell metaphase without MycER™-activation; Panel E: PreB metaphase 30 hours after MycER™-activation; Panel F: Ba/F3 cells without Δ106-MycER™-activation; Panel G: Ba/F3 cells 30 hours after Δ106-MycER™-activation. In each panel, (a) represents the dual color FISH hybridization signals of telomeres (red) and centromeres (green); in each panel, (b) shows the centromeric signals (green) only, and (c) the telomeric signals (red) only. Arrows point to Rb chromosomes in Panels B, C, and E. A white box is drawn around Rb chromosomes of each of the panels B, C and E. The Rb chromosome that is highlighted in this manner is then enlarged and shown in the zoomed image at the bottom of each of these panels in dual color (left), green (centromere) (middle), and red (telomere) (right) to pinpoint telomere-centromere-fusions. These are also illustrated by arrows.
Figure 6A:
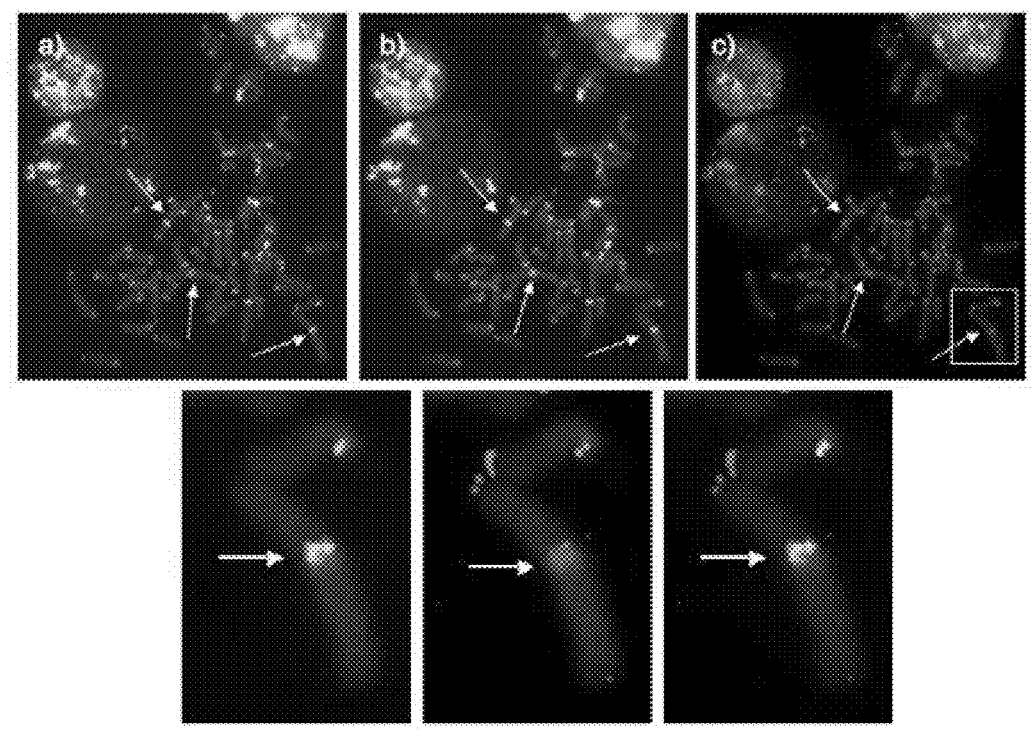
Figure 6B:
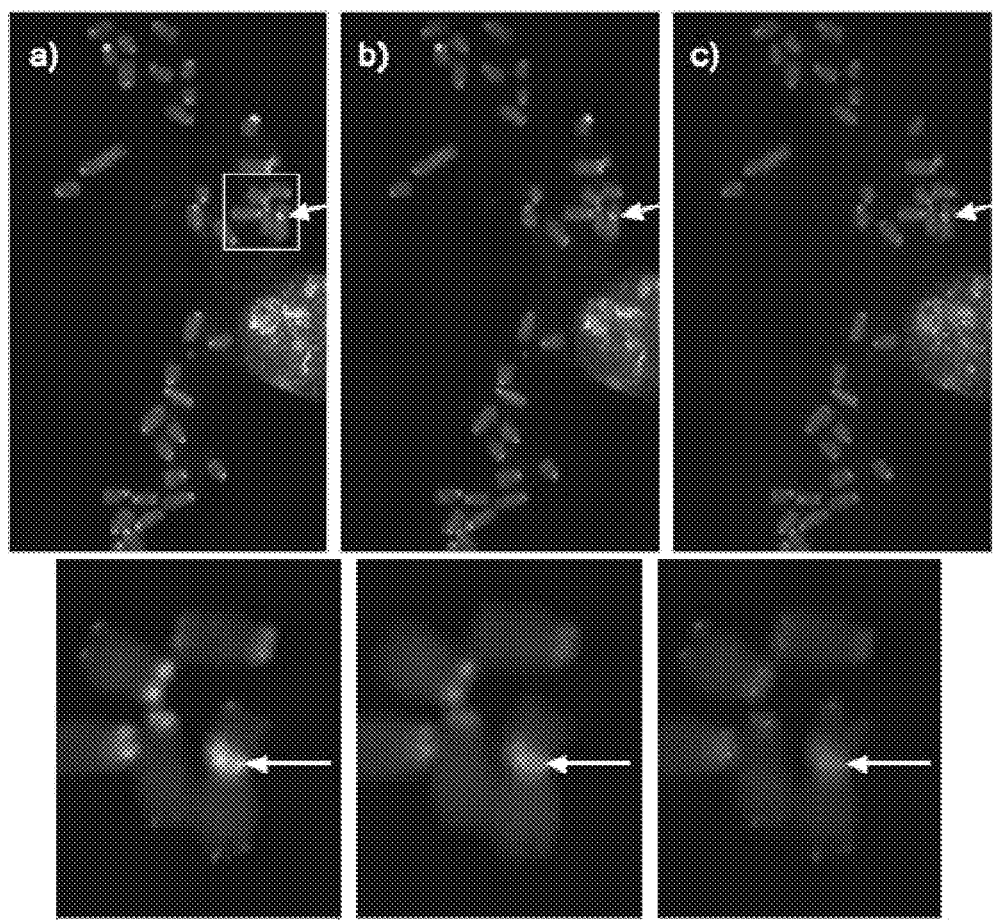
Figure 6C:
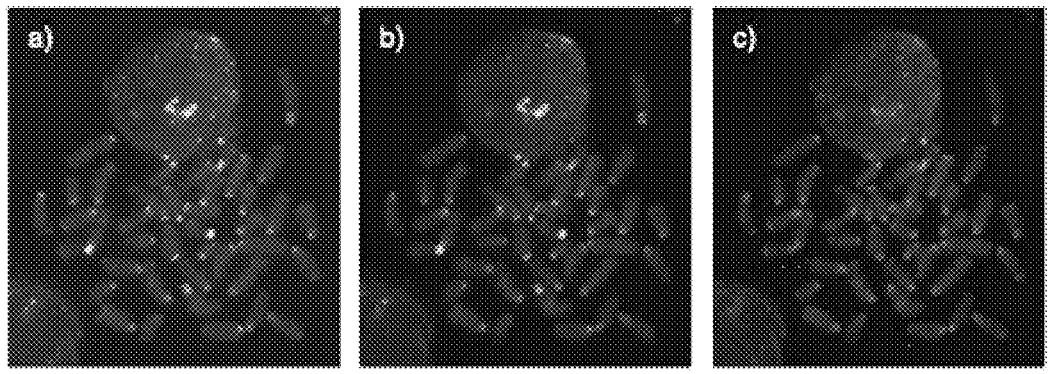
Figure 6C:
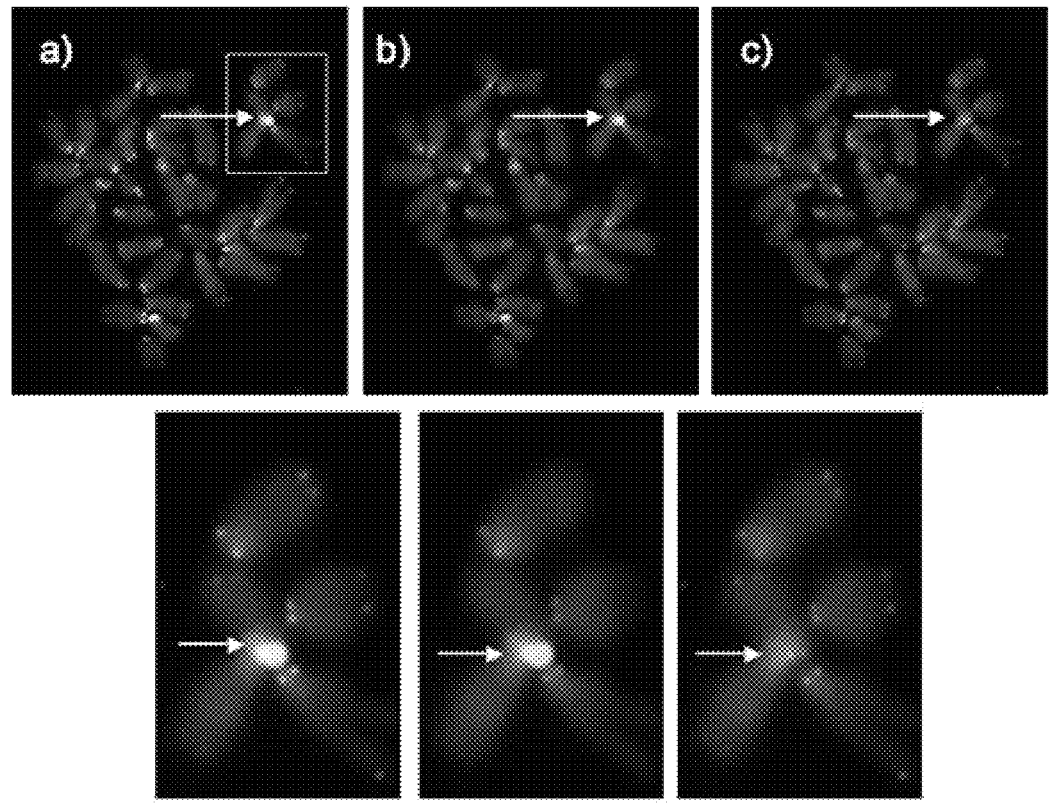
Figure 6D:
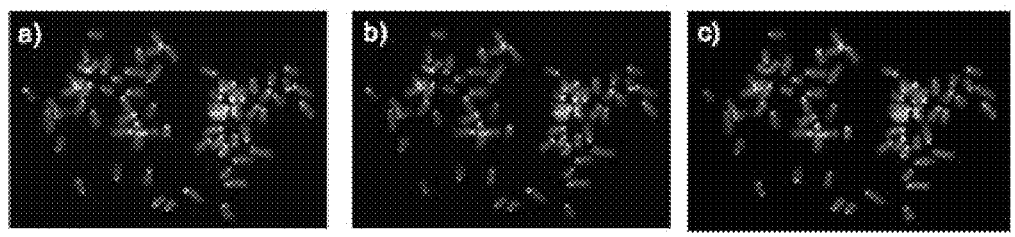
Figure 6D:
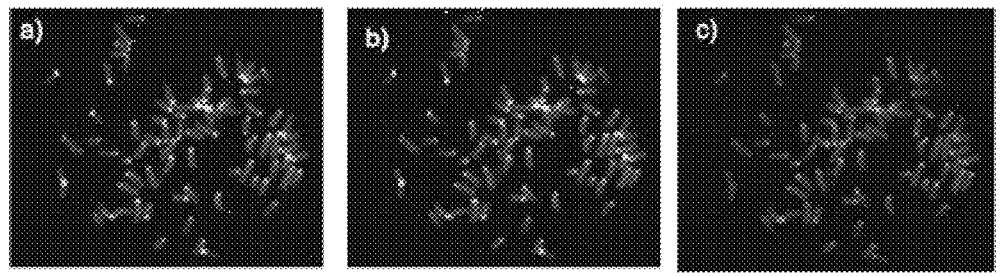

The 3D nuclear distribution frequencies of centromeres are significantly changed during the process of immortalization and malignant transformation. Centromeres assume higher distribution frequencies towards central nuclear positions in tumor cells than in immortalized and normal cells [Sarkar R, Guffei A, Vermolen B J, Garini Y, Mai S. Centromere positions in normal, immortalized and malignant B cells. 2006 Submitted]. To investigate whether such alterations in the 3D organization of centromeres have a consequence for the structural organization of chromosomes, the inventors analyzed the nuclear organization of centromeres and telomeres in primary, immortalized and tumor cells (Table 1; FIG. 4). These data suggested a role for c-Myc in nuclear remodeling of centromeres and telomeres (FIG. 4). Therefore, the impact of c-Myc was examined on the formation of Robertsonian (Rb) chromosomes, a structural chromosomal aberrations involving centromeres (FIGS. 5 and 6, Tables 1 and 2).

FIG. 4 highlights representative images of primary, immortalized and tumor cells in the absence or presence of constitutive or conditional wild-type or myc box II-deletion mutant, Δ106, Myc expression (Table 1). After dual color hybridization with centromeres (green) and telomeres (red), nuclei of primary lymphocytes and immortalized PreB cells show a predominantly peripheral organization of centromeres; their telomeres are found throughout the nuclear space (FIG. 4, Panels A and B). In contrast to this nuclear organization, nuclei of MOPC460D tumor cells with constitutive deregulation of c-Myc protein due to T(12;15) exhibit a more central nuclear distribution of centromeres (FIG. 4, Panel C). Their telomeres (red) are shorter, and some are found in close association with centromeres (FIG. 4, Panel C, arrow). Each acrocentric mouse chromosome is expected to have four telomeres, i.e. two at each end of the long arm and two at the short, centromeric end of a chromosome. Therefore, the hybridization signals of telomeres and centromeres in mouse interphase nuclei would be telomere (red)-centromere (green)- and free telomere signals (red) due to their location at the end of the long arm of the chromosome and distant from the centromere (see cartoon in FIG. 4, Panel A). The nuclear telomere-centromere-telomere (TCT) signals may also touch each other if a chromosome is bent. The data shows that primary mouse lymphocytes show the expected TCT signals (FIG. 4, Panel A). Similarly, immortalized PreB cells exhibit TCT signals (FIG. 4, Panel B). However, nuclei of MOPC460D cells display a different organization; TCT signals are sometimes switched to centromere (green)-telomere (red)-centromere (green) (CTC) signals, suggesting a centromere-centromere association with telomeric signals bridging the centromeres (FIG. 4, Panel C, arrow and cartoon). To examine the 3D distribution patterns of centromeres and telomeres in conditionally Myc expressing cells, PreB cells, stably transfected with MycER™ were studied. FIG. 4 (Panels D and E) illustrates the data obtained for PreB cells in the absence of MycER™-activation (Panel D) and in its presence (Panel E). The nuclear organization of CTC is apparent only after MycER™-activation (FIG. 4, in Panel E, arrow and cartoon) suggesting a Myc-dependent nuclear remodeling of centromeres. To verify the Myc-dependency of this process, a myc box II deletion mutant Δ106-MycER™ was tested under identical conditions (FIG. 4, Panels F and G). Δ106-MycER™ was unable to induce the nuclear remodeling of centromeres, and no CTCs were found (FIG. 4, Panels F and G and cartoon). In conclusion, the formation of CTCs is dependent on the presence of Myc and on the presence of myc box II.

c-Myc and myc boxII-Dependent Formation Of Robertsonian Chromosomes

The analysis of TCT vs. CTC signals in 3D images is complex, and not all potential CTCs will be found due to the clustering of centromeres at the nuclear periphery [see also Sarkar R et al. (2006); Solovei I et al. (2004); Weierich C et al. (2003)]. The inventors therefore decided to tackle the question of centromere remodeling by molecular cytogenetics. Using this approach, the inventors investigated whether the altered nuclear organization of centromeres impacted on the structural organization of chromosomes, particularly on the formation of Robertsonian (Rb) chromosomes. In Rb chromosomes, acrocentric chromosomes become bi-armed due to the fusions of centromeres of the two individual acrocentric chromosomes. To address the question of Rb chromosome formation in our cell models, spectral karyotyping (SKY) of primary lymphocytes, MOPC460D, PreB cells with and without MycER™-activation, and of BaF/3 cells in the presence or absence of Δ106-MycER™-activation were performed (Table 1 and FIG. 5). Twenty metaphases were examined for each cell type. In contrast to primary lymphocytes of T38HxBalb/c mice that did not exhibit Rb chromosomes (FIG. 5, Panel A), MOPC460D tumor cells showed significant numbers of Rb chromosomes per metaphase (p<0.0001): Fifteen out of 20 MOPC460D metaphases showed one or more Rb chromosomes; twenty six Rb chromosomes were observed in 15 metaphases (FIG. 5, Panel B, arrows). It is noteworthy that MOPC460D cells displayed a non-random involvement of specific chromosomes in the formation of Rb chromosomes, such as chromosomes 1, 3, 8, 14, 15, 17 and X (Table 2). Out of these, chromosome 15 was most frequent (found 24 times in Rb fusions in the 15 Rb chromosome-carrying metaphases), followed by chromosomes 1 and 14 (found 21 times in 15 Rb chromosome-carrying metaphases) (Table 2).

To analyze the impact of Myc on the formation of Rb chromosomes, PreB cells were used and studied in the absence and presence of MycER™-activation (FIG. 5, Panels C and D, respectively). While non-MycER™-activated PreB cells did not exhibit Rb chromosomes (FIG. 5, Panel C), MycER™-activated PreB cells showed the Myc-dependent formation of Rb chromosomes. Thirty-three percent of metaphases (⁶⁄₂₀) showed the formation of Rb chromosomes within 30 hours (FIG. 5, Panel D, arrows, (p=0.02). During this observation period, we did not note specific chromosome combinations that were involved in the formation of Rb chromosomes.

The Myc-dependency of this structural chromosomal change was confirmed with the myc box II deletion mutant, Δ106. The conditional expression of Δ106-MycER™ did not lead to the formation of Rb chromosomes in Ba/F3 cells (FIG. 5, Panels E and F respectively). The data indicate that; i) the nuclear centromere organization impacts on chromosomal structure and that ii) Myc deregulation leads to the formation of Rb chromosomes in a myc box II-dependent manner.

Rb Chromosomes Form Through Centromere-Telomere-Fusions in a Myc-Dependent Manner Using dual color fluorescent in situ hybridization with centromeres and telomeres on metaphase chromosomes, the inventors next examined whether or not the Rb chromosomes seen displayed centromere-telomere-fusions. Using the cell lines listed in Table 1, 20 metaphases per cell type were analyzed and the presence of telomeric signals at the fusion points of centromeres in Rb fusion chromosomes were determined (FIG. 6). The presence of telomeric hybridization signals on Rb chromosomes formed after MycER™-activation were noted in PreB cells (FIG. 6, Panel E, arrows and zoomed images), in MOPC460D cells (FIG. 6, Panel B, arrows and zoomed images), and in a primary mouse plasmacytoma (FIG. 6, Panel C, arrows and zoomed images). In contrast, no Rb chromosomes were seen in primary lymphocytes (FIG. 6, Panel A), in non-MycER™-activated PreB cells (FIG. 6, Panel D), or in Δ106-MycER™-activated and control Ba/F3 cells (FIG. 6, Panels G and F respectively). In conclusion, constitutive or conditional wildtype Myc deregulation, but not deregulated Δ106-Myc protein expression lead to the formation of Rb chromosomes that carry telomeric signals at their fusion points.

Discussion

Rb Chromosomes in Different Species and in Cancer

Robertsonian (Rb) chromosomes represent structural genetic changes that occur in many species including plants [Friebe B, Zhang P, Linc G, Gill B S. (2005) *Cytogenet Genome Res* 109:293-297], cattle [Mastromonaco G F, Coppola G, Crawshaw G, DiBerardino D, King W A. (2004) *Chromosome Research* 12:725-731], some strains of mice [Gazave E, Catalan J, Ramalhinho Mda G, Mathias Mda L, Nunes A C, Dumas D, Britton-Davidian J, Auffray J C. (2003) *Genet Res, Camb* 81:33-42; Nachman M W and Searle J B. (1995) *Trends Ecol Evol* 10:397-402], fish [Gold J R, Gall G A. (1975) *Can J Genet Cytol* 17:41-53], and in humans [Welborn, J. (2004) *Cancer Gent Cytogenet* 151:14-35]. In humans, such Rb chromosomes are among the common structural aberrations in aborted fetuses and in newborns [Jacobs P A. (1981) *Am J Hum Genet.* 33:44-54; Nielsen J, Wohlert M. (1991) *Hum Genet* 87:81-83]. Moreover, Rb chromosomes in humans have been found as acquired or constitutional genetic lesions in hematological cancers [Welborn, J. (2004); Qian J, Xue Y, Sun J, Guo Y, Pan J, Wu Y, Wang W, Yao L. (2002) *Cancer Gent Cytogenet* 132:79-80] and in solid tumors [Padilla-Nash H M, Heselmeyer-Haddad K, Wangsa D, Zhang H, Ghadimi B M, Macville M, Augustus M, Schrock E, Hilgenfeld E, Ried T. (2001) *Genes Chromosomes Cancer* 30:349-363; Bayani J, Zielenska M, Pandita A, Al-Romaih K, Karaskova J, Harrison K, Bridge J A, Sørensen P, Thorner P, Squire J A. (2003) *Genes Chromosomes Cancer* 36:7-16]. In addition, they have been reported at the onset of acute myelogenous leukemia [Shimokawa T, Sakai M, Kojima Y, Takeyama H. (2004) *Internal Medicine* 43:508-511]. The finding of non-random Rb chromosomes in cultured or in in vivo selected mouse cells is not unprecedented. Minarovits et al. [Minarovits J, Steinitz M, Boldog F, Imreh S, Wirschubsky Z, Ingvarsson S, Hedenskog M, Minarovits-Kormuta S, Klein G. (1990) *Int J Cancer* 45:514-520] reported for ascites-converted murine sarcoma sublines that 25 to 40% of the examined metaphases in the sublines contained Rb(1;5) and 3545% of the examined metaphases had Rb(5;5). Their study suggests that chromosome 5 and 1 were non-randomly involved in these fusions. Rb fusions in an ascitic cell line was also reported by Chakrabarti and Chakrabarti [Chakrabarti S, Chakrabarti A. (1977) *Experientia* 33:1296-1297]. An early study on mouse in vitro cultures A9 and B82 cell lines identified a set of Rb chromosomes, without giving details about their (non)randomness [Russell M H, Engel E, Vaughn W K, McGee B J. (1977) *J Cell Sci* 25:59-71]. The non-random nature of such Rb fusions has been seen in vivo, in the house mouse [Gazave E et al. (2003)]. Furthermore, genotoxic treatments, such as X-ray, are a potent inducer of Rb fusions in mouse cells [Boei J J, Natarajan A T. (1996) *Int J Radiat Biol* 69:421-427].

Rb Chromosomes Form in c-Myc and myc box II-Dependent Manner

The present data shows that mouse plasmacytoma cells (MOPC460D) in long-term culture develop significant numbers of Rb chromosomes. Specific Rb chromosomes are found more frequently than others. For example, chromosomes 1, 3, 8, 14, 15, 17, and X are involved in Rb translocations almost all the time although with different individual frequencies (Table 2). It is possible that the non-random composition of Rb fusions was selected for during long-term culture in combination with constitutively elevated levels of c-Myc protein in these cells. In contrast, a single MycER™-activation in PreB cells led to the formation of Rb chromosomes but these Rb chromosomes did not show non-random fusion chromosome partners over the 42 hours investigated. Of note, also PCT1G1, a primary plasmacytoma, that displayed Rb chromosomes (Table 1, FIG. 6), did not show a non-random constitution of Rb chromosomes.

This study shows that c-Myc deregulation in diploid immortalized PreB cells induces the formation of Rb chromosomes. Moreover, this effect of c-Myc is dependent on the presence of myc box II. Δ106-Myc-containing Ba/F3 cells do not form Rb chromosomes upon Myc activation. Rb chromosomes were previously seen in Rat1A-MycER cells upon Myc activation [Mai S, Fluri M, Siwarski D, Huppi K. (1996) Chromosome Res 4:365-371; Felsher D W, Bishop J M. (1999) Proc Natl Acad Sci USA 96:3940-3944] and in transgenic MMTV-myc/p53 mice: For example, one of the primary tumors that formed in these mice, 67a5, contained Rb(X;15) and Rb (11;15) [McCormack S J, Weaver Z, Deming S, Natarajan G, Torri J, Johnson M D, Liyanage M, Ried T, Dickson R B. (1998) Oncogene 16:2755-2766]. Furthermore, Rb chromosomes are common in a model of mouse skin tumorgenesis with c-Myc deregulation.

Does it Matter to have De Novo Rb Chromosomes in a Cell?

One could assume that Rb chromosomes merely remodel the nuclear organization, thereby placing two chromosomes into a 'forced' unit and into a new nuclear position or environment, without any further impact on the cell. Several lines of evidence suggest, however, that this new fused entity can be different and that the remodeling of two acrocentric chromosomes into one Rb chromosome may possibly have wide-ranging effects. For example, it has been described that the formation of an Rb chromosome suppresses somatic recombination [Haigis K M, Dove W F. (2003) Nat Genet. 33:33-39. Epub Nov. 25, 2002]. Another study linked Rb chromosomes to altered nuclear architecture and subfertility in mice [Garagna S, Zuccotti M, Thornhill A, Fernandez-Donoso R, Berrios S, Capanna E, Redi C A. (2001) J Cell Sci 114(Pt 24): 4429-4434]. Finally, it has been shown that the type of c-myc-activating chromosomal translocations in mouse plasmacytoma is altered in Rb(6;15)-carrying mice [Silva S, Wiener F, Klein G, Janz S. (2005) Genes Chromosomes Cancer 42:416-426]. These findings suggest that a nuclear organization of single chromosomes into Rb chromosomes may have a broad impact on the overall physiological state of Rb-carrying cells, on the function of the organism and on oncogenesis.

Mechanisms of Rb Chromosome Formation

Previous studies have suggested that Rb chromosomes form after recombination [Hecht F, Morgan R, Hecht, B. K. (1988) Cancer Genet Cytogenet 35:79-81; Kalitsis P, Girffiths B, Choo A K H. (2006) Proc Natl Acad Sci USA 103: 8786-8791], centric mis-division and rejoining [Friebe B et al. (2005)] or fusion [Slijepcevic P. (1998) Chromosoma 107: 136-140]. Our data support the concept of fusion, but add a new dimension: Rb fusions can be initiated by c-Myc onco-gene deregulation. After c-Myc deregulation, Rb chromosomes are generated when centromeric telomeres of mouse acrocentric chromosomes fuse. This telomeric fusion is a direct consequence of the recently described Myc-dependent formation of telomeric aggregates [Louis S F et al. (2005)] and of nuclear remodeling of centromeres [this study and Sarkar R et al. (2006)]. In this context, c-Myc-induced telomeric aggregates will lead to end-to-end fusions of telomeres on both ends of the chromosomes. Acrocentric telomere fusions will generate Rb chromosomes, while telomeric fusions of the long arms of two chromosomes will create dicentric chromosomes. The latter usually initiate BBF cycles, which we described recently [Louis S F et al. (2005)]. Theoretically, this fusion process does not require additional mechanisms. However, it is likely that c-Myc's ability to induce DNA breaks [Vafa O, Wade M, Kern S, Beeche M, Pandita T K, Hampton G M, Wahl G M. (2002) Mol Cell 9:1031-1044; Karlsson A, Deb-Basu D, Chemy A, Turner S, Ford J, Felsher D W. (2003) Proc Natl Acad Sci USA 100: 9974-9. Epub Aug. 8, 2003; Ray S, Atkuri K R, Deb-Basu D, Adler A S, Chang H Y, Herzenberg L A, Felsher D W. (2006) Cancer Res 66:6598-6605] may initiate another molecular pathway of Rb chromosome formation. Whether the latter mechanism would act alone or in concert with the former is currently unknown. The requirement of myc box II for Rb chromosome formation confirms that the process of Rb chromosome formation is Myc-dependent and involves telomeric fusions [Caporali A et al. (2006)]. The present study opens new avenues into investigations about myc box II-related Myc-cooperating proteins that may play a role in this Myc-induced nuclear remodeling of centromeres.

While the present invention has been described with reference to what are presently considered to be the preferred examples, it is to be understood that the invention is not limited to the disclosed examples. To the contrary, the invention is intended to cover various modifications and equivalent arrangements included within the spirit and scope of the appended claims.

All publications, patents and patent applications are herein incorporated by reference in their entirety to the same extent as if each individual publication, patent or patent application was specifically and individually indicated to be incorporated by reference in its entirety.

LIST OF REFERENCES

Bayani J, Zielenska M, Pandita A, Al-Romaih K, Karaskova J, Harrison K, Bridge J A, Sorensen P, Thorner P, Squire J A. (2003) Genes Chromosomes Cancer 36:7-16.

Boei J J, Natarajan A T. (1996) Int J Radiat Biol 69:421-427.

Caporali A, Wark L, Vermolen B J, Garini, Y., Mai S: Telomeric aggregates and end-to-end chromosomal fusions require my box II. (2006) Oncogene In press.

Chakrabarti S, Chakrabarti A. (1977) Experientia 33:1296-1297.

Chuang T C, Moshir S, Garini Y, Chuang A Y, Young I T, Vermolen B, van den Doel R, Mougey V, Perrin M, Braun M, Kerr P D, Fest T, Boukamp P, Mai S: The three-dimensional organization of telomeres in the nucleus of mammalian cells. (2004) BMC Biol 3:2-12.

Felsher D W, Bishop J M. (1999) Proc Natl Acad Sci USA 96:3940-3944.

Fest T, Mougey V, Dalstein V, Hagerty M, Milette D, Silva S, Mai S. (2002) Oncogene 21:2981-2990.

Fest T, Guffei A, Williams G, Silva S, Mai S. (2005) Oncogene 24:2944-2953.

Friebe B, Zhang P, Linc G, Gill B S. (2005) *Cytogenet Genome Res* 109:293-297.

Garagna S, Zuccotti M, Thornhill A, Fernandez-Donoso R, Berrios S, Capanna E, Redi C A. (2001) *J Cell Sci* 114(Pt 24):4429-4434.

Garagna S, Merico V, Sebastiano V, Monti M, Orlandini G, Gatti R, Scandroglio R, Redi C A, Zuccotti M: Three-dimensional localization and dynamics of centromeres in mouse oocytes during folliculogenesis. (2004) *J Mol Histol* 35:631-638.

Gazave E, Catalan J, Ramalhinho Mda G, Mathias Mda L, Nunes A C, Dumas D, Britton-Davidian J, Auffray J C. (2003) *Genet Res Camb* 81:33-42.

Gold J R, Gall G A. (1975) *Can J Genet Cytol* 17:41-53.

Haigis K M, Dove W F. (2003) *Nat Genet* 33:33-39. Epub Nov. 25, 2002.

Hecht F, Morgan R, Hecht, B. K. (1988) *Cancer Genet Cytogenet* 35:79-81.

Jacobs P A. (1981) *Am J Hum Genet.* 33:44-54.

Kalitsis P, Girffiths B, Choo A K H. (2006) *Proc Natl Acad Sci USA* 103:87868791.

Karlsson A, Deb-Basu D, Chemy A, Turner S, Ford J, Felsher D W. (2003) *Proc Natl Acad Sci USA* 100:9974-9. Epub Aug. 8, 2003.

Kuschak T I, Kuschak B C, Taylor C L, Wright J A, Wiener F, Mai S: c-Myc initiates illegitimate replication of the ribonucleotide reductase R2 gene. (2002) *Oncogene* 21:909-920.

Louis, S F, Vermolen B J, Garini Y, Young I T, Guffei A, Lichtensztejn Z, Kuttler F, Chuang T C, Moshir S, Mougey V, Chuang A Y, Kerr P D, Fest T, Boukamp P, Mai S: c-Myc induces chromosomal rearrangements through telomere and chromosome remodeling in the interphase nucleus. (2005) *Proc Natl Acad Sci USA* 102:9613-9618.

Mai S, Fluri M, Siwarski D, Huppi K. (1996) *Chromosome Res* 4:365-371.

Mai S, Hanley-Hyde J, Rainey G J, Kuschak T I, Paul J T, Littlewood T D, Mischak H, Stevens L M, Henderson D W, Mushinski J F: Chromosomal and extrachromosomal instability of the cyclin D2 gene is induced by Myc overexpression. (1999) *Neoplasia* 1:241-252.

Mai S, Garini Y: Oncogenic remodeling of the three-dimensional organization of the interphase nucleus: c-Myc induces telomeric aggregates whose formation precedes chromosomal rearrangements. (2005) *Cell Cycle* 4:1327-1331. Epub Oct. 5, 2005.

Mai S and Garini Y: The significance of telomeric aggregates in the interphase nuclei of tumor cells. (2006) *J Cell Biochem* 97:904-915. Review.

Mastromonaco G F, Coppola G, Crawshaw G, DiBerardino D, King W A. (2004) *Chromosome Research* 12:725-731.

McCormack S J, Weaver Z, Deming S, Natarajan G, Torri J, Johnson M D, Liyanage M, Ried T, Dickson R B. (1998) *Oncogene* 16:2755-2766.

Minarovits J, Steinitz M, Boldog F, lmreh S, Wirschubsky Z, Ingvarsson S, Hedenskog M, Minarovits-Kormuta S, Klein G. (1990) *Int J Cancer* 45:514-520.

Nachman M W and Searle J B. (1995) *Trends Ecol Evol* 10:397-402.

Nielsen J, Wohlert M. (1991) *Hum Genet* 87:81-83.

Padilla-Nash H M, Heselmeyer-Haddad K, Wangsa D, Zhang H, Ghadimi B M, Macville M, Augustus M, Schrock E, Hilgenfeld E, Ried T. (2001) *Genes Chromosomes Cancer* 30:349-363.

Qian J, Xue Y, Sun J, Guo Y, Pan J, Wu Y, Wang W, Yao L. (2002) *Cancer Gent Cytogenet* 132:79-80.

Ray S, Atkuri K R, Deb-Basu D, Adler A S, Chang H Y, Herzenberg L A, Felsher D W. (2006) *Cancer Res* 66:6598-6605.

Ridler T W and Calvard, S: Picture thresholding using an iterative selection method. (1978) *IEEE Trans on Systems, Man, and Cybernetics*, SMC-8(8):630-632.

Russell M H, Engel E, Vaughn W K, McGee B J. (1977) *J Cell Sci* 25:59-71.

Sarkar R, Guffei A, Vermolen B J, Garini Y, Mai S. Centromere positions in normal, immortalized and malignant B cells. (2006) Submitted.

Schaefer L H, Schuster D. and Herz H: Generalized approach for accelerated maximum likelihood based image restoration applied to three-dimensional fluorescence microscopy. (2001) *J Microsc* 204:99-107.

Shimokawa T, Sakai M, Kojima Y, Takeyama H. (2004) *Internal Medicine* 43:508-511.

Silva S, Wiener F, Klein G, Janz S. (2005) *Genes Chromosomes Cancer* 42:416-426.

Slijepcevic P. (1998) *Chromosoma* 107:136-140.

Solovei I, Schermelleh L, During K, Engelhardt A, Stein S, Cremer C, Cremer T: Differences in centromere positioning of cycling and postmitotic human cell types. (2004) *Chromosoma* 112:410-423. Epub Jun. 9, 2004.

Vafa O, Wade M, Kern S, Beeche M, Pandita T K, Hampton G M, Wahl G M. (2002) *Mol Cell* 9:1031-1044.

Welborn, J. (2004) *Cancer Gent. Cytogenet* 151:14-35.

Weierich C, Brero A, Stein S, von Hase J, Cremer C, Cremer T, Solovei I: Three-dimensional arrangements of centromeres and telomeres in nuclei of human and murine lymphocytes. (2003) *Chromosome Res* 11:485-502.

Wiblin A E, Cui W, Clark A J, Bickmore W A: Distinctive nuclear organisation of centromeres and regions involved in pluripotency in human embryonic stem cells. (2005) *J Cell Sci* 118(Pt 17):3861-3868. Epub Aug. 16, 2005.

Zink D, Fischer A H, Nickerson J A: Nuclear structure in cancer cells. (2004) *Nat Rev Cancer* 4:677-687.

TABLE 1

Table 1. List of cells used in this study.
More details on these cells can be found in Methods and in the accompanying references.

| CELLS STUDIED | CHARACTERISTICS |
|---|---|
| Primary mouse lymphocytes | diploid |
| Immortalized PreB cells carrying MycER ™ | diploid, non tumorigenic in the absence of MycER ™-activation (44, 6) |
| Plasmacytoma cell line MOPC460 | near tetraploid, T(12, 15), tumorigenic (6) |
| Primary plasmacytoma PCT1G1 | near tetraploid, v-abl/myc-induced, tumorigenic (unpublished data) |
| Immortalized proB cells (Ba/F3) carrying MycER ™ | tetraploid, non tumorigenic (12, 13) tetraploid, tumorigenic only in the presence of MycER ™-activation (12, 13) |
| carrying myc box II-deletion mutant Δ106-MycER ™ | tetraploid, non tumorigenic in the presence or absence of Δ106-MycER ™ activation (12, 13) |

TABLE 2

Table 2. Summary of chromosomes participating in the formation of Rb chromosomes in MOPC460D cells in a non-random manner. The numbers given are derived from the analysis of 20 metaphases. Fifteen out of these 20 metaphases carried one or more Rb chromosomes. The involvement of each chromosome in the formation of Rb chromosomes is given and the respective significance is indicated. For details, see text and Methods.

| Chromosome number | Times involved in Rb fusions | p value |
|---|---|---|
| 1 | 21 | <0.0001 |
| 3 | 11 | 0.001 |
| 8 | 18 | <0.0001 |
| 14 | 21 | <0.0001 |
| 15 | 24 | <0.0001 |
| 17 | 14 | 0.0001 |
| X | 11 | 0.001 |

We claim:

1. A quantitative method of detecting or monitoring cancer in a test cell from a subject comprising the steps:
   (a) characterizing centromere organization in the test cell using three-dimensional (3D) analysis comprising:
      (i) inputting image data of the 3D organization of centromeres;
      (ii) processing the image data using an image data processor to find a set of coordinates $\{(x_i,y_i,z_i)\}$, i=1, . . . , N, where $(x_i, y_i, z_i)$ is a position of the $i^{th}$ centromere, the processing comprising segmenting the centromeric region using a first threshold to segment the centromeric region from background and a second threshold to segment proximal centromeric regions from one another;
      (iii) finding 1: a set of distances $\{d_i\}$, i=1, . . . , N, where $d_i$ is the distance between $(x_i,y_i,z_i)$ and a nuclear centre or a nuclear border, 2: a set of volumes of the centromeres and/or set of intensities of the centromeres, wherein the set of $\{d_i\}$, volumes and/or the intensity is utilized to characterize the centromere 3D organization; and
   (b) comparing a distribution of the distances between the centromeres and the nuclear centre or nuclear border of the test cell with a distribution of distances between the centromeres and the nuclear centre or nuclear border of a control cell having the same lineage as the test cell, wherein the comparison between the distribution of centromere distances of the test cell and the distribution of centromere distances of the control cell is used to detect or monitor cancer.

2. The method according to claim 1, wherein the 3D analysis is high-resolution 3D microscopy.

3. The method according to claim 1, wherein the distribution of the distances between the centromere and the nuclear center and/or nuclear border is analyzed by: segmenting the centromeric region of the test cell; calculating the center of mass of each segmented region using intensity of each voxel in the region; and calculating the Euclidean distance between the center of mass of each segmented region and the nuclear center and/or border.

4. The method according to claim 3, wherein the center of mass of each segmented region is calculated using position coordinates in three-dimensional space weighted by the intensity of each corresponding voxel.

5. The method according to claim 1, wherein the control cell is a normal disease-free cell and a difference in centromere organization in the test cell compared to the control cell is indicative of cancer.

6. The method according to claim 1, wherein the centromere organization is characterized in any phase of the cell cycle and the phase of the cell cycle is taken into account for the analysis.

7. The method according to claim 1, wherein the cancer is lymphoma, plasmacytoma or cMyc-dependent cancer.

8. The method of claim 1, further comprising providing the subject with a prognosis of cancer when detecting centrally located centromeres in the nucleus of the test cell as compared to the centromeres of the control cell.

9. The method of claim 8, further comprising providing the subject with a prognosis of not cancer when detecting peripherally located centromeres in the nucleus of the test cell as compared to the centromeres of the control cell.

10. A method of monitoring cancer treatment in a test cell from a subject comprising the steps:
    (a) characterizing centromere organization in the test cell using three-dimensional (3D) analysiscomprising:
       (i) inputting image data of the 3D organization of centromeres;
       (ii) processing the image data using an image data processor to find a set of coordinates $\{(x_i,y_i,z_i)\}$, i=1, . . . , N, where $(x_i, y_i, z_i)$ is a position of the $i^{th}$ centromere, the processing comprising segmenting the centromeric region using a first threshold to segment the centromeric region from background and a second threshold to segment proximal centromeric regions from one another;
       (iii) finding 1: a set of distances $\{d_i\}$, i=1, . . . , N, where $d_i$ is the distance between $(x_i,y_i,z_i)$ and a nuclear centre or a nuclear border, 2: a set of volumes of the centromeres and/or set of intensities of the centromeres, wherein the set of $\{d_i\}$, volumes and/or the intensity is utilized to characterize the centromere 3D organization; and
    (b) comparing a distribution of the distances between the centromeres and the nuclear centre or nuclear border of the test cell with a distribution of distances between the centromeres and the nuclear centre or nuclear border of a control cell having the same lineage as the test cell, wherein the comparison between the distribution of centromere distances of the test cell and the distribution of centromere distances of the control cell is correlated with cancer treatment.

11. The method according to claim 10, wherein the 3D analysis is high-resolution 3D microscopy.

12. The method according to claim 10, wherein the distribution of the distances between the centromere and the nuclear center and/or nuclear border is analyzed by: segmenting the centromeric region of the test cell; calculating the center of mass of each segmented region using intensity of each voxel in the region; and calculating the Euclidean distance between the center of mass of each segmented region and the nuclear center and/or border.

13. The method of claim 12, wherein the center of mass of each segmented region is calculated using position coordinates in three-dimensional space weighted by the intensity of each corresponding voxel.

14. The method according to claim 10, wherein the centromere organization is characterized in any phase of the cell cycle and the phase of the cell cycle is taken into account for the analysis.

15. The method according to claim 10, wherein the cancer is lymphoma, plasmacytoma or cMyc-dependent cancer.

16. The method of claim 10, further comprising providing the subject with an indication of unsuccessful therapy when detecting centrally located centromeres in the nucleus of the test cell as compared to the centromeres of the control cell.

17. The method of claim 16, further comprising providing the subject with an indication of successful therapy when detecting peripherally located centromeres in the nucleus of the test cell as compared to the centromeres of the control cell.

18. A non-transitory computer-readable medium upon which a plurality of instructions are stored, the instructions for performing the steps of the method as claimed in claim 1.

19. A non-transitory computer-readable medium upon which a plurality of instructions are stored, the instructions for performing the steps of the method as claimed in claim 10.

* * * * *